United States Patent
Sutradhar et al.

(10) Patent No.: US 8,999,021 B2
(45) Date of Patent: Apr. 7, 2015

(54) METHODS FOR GASIFICATION OF CARBONACEOUS MATERIALS

(75) Inventors: Bhagya Chandra Sutradhar, Aurora, IL (US); Ching-Whan Ko, Fayetteville, AR (US)

(73) Assignee: Ineos USA LLC, Lisle, IL (US)

( * ) Notice: Subject to any disclaimer, the term of this patent is extended or adjusted under 35 U.S.C. 154(b) by 756 days.

(21) Appl. No.: 12/798,831

(22) Filed: Apr. 13, 2010

(65) Prior Publication Data

US 2011/0250661 A1    Oct. 13, 2011

(51) Int. Cl.
| | |
|---|---|
| *C01B 3/36* | (2006.01) |
| *C10J 3/00* | (2006.01) |
| *C10J 3/72* | (2006.01) |
| *C12P 7/06* | (2006.01) |
| *C12P 7/08* | (2006.01) |

(52) U.S. Cl.
CPC ... *C10J 3/00* (2013.01); *C01B 3/36* (2013.01); *C01B 2203/025* (2013.01); *C10J 3/721* (2013.01); *C10J 2300/0956* (2013.01); *C10J 2300/0959* (2013.01); *C10J 2300/0989* (2013.01); *C10J 2300/1665* (2013.01); *C10J 2300/1681* (2013.01); *C12P 7/065* (2013.01); *C12P 7/08* (2013.01); *Y02E 50/32* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 3,980,592 A | | 9/1976 | Marion |
| 4,017,271 A | * | 4/1977 | Barclay et al. ............. 48/197 R |
| 4,277,365 A | * | 7/1981 | Paull et al. ................. 252/373 |
| 4,381,187 A | * | 4/1983 | Sederquist .................. 48/212 |
| 4,399,314 A | * | 8/1983 | Child ........................ 208/391 |
| 4,597,771 A | * | 7/1986 | Cheng ......................... 48/77 |
| 6,269,286 B1 | * | 7/2001 | Tse et al. ................... 700/271 |
| 6,423,116 B1 | * | 7/2002 | Ottow ........................ 75/503 |
| 6,595,001 B2 | | 7/2003 | Rautenbach |
| 7,285,402 B2 | | 10/2007 | Gaddy et al. |
| 7,923,476 B2 | | 4/2011 | Young |
| 7,932,298 B2 | | 4/2011 | Young |
| 2007/0151155 A1 | * | 7/2007 | Ploeg et al. ................. 48/210 |
| 2007/0266634 A1 | | 11/2007 | Tsangaris et al. |
| 2008/0115415 A1 | * | 5/2008 | Agrawal et al. ............. 48/101 |
| 2008/0169449 A1 | | 7/2008 | Mundschau |
| 2008/0209807 A1 | | 9/2008 | Tsangaris et al. |

(Continued)

FOREIGN PATENT DOCUMENTS

| | | |
|---|---|---|
| WO | 93/18341 | 9/1993 |
| WO | 2007/112101 | 10/2007 |

(Continued)

OTHER PUBLICATIONS

Houben et al., Tar Reduction through Partial Combustion of Fuel Gas, Fuel 84(2005): 817-824.

*Primary Examiner* — Imran Akram
(74) *Attorney, Agent, or Firm* — Ineos USA LLC

(57) ABSTRACT

The present disclosure is generally directed to process of gasification of carbonaceous materials to produce synthesis gas or syngas. The present disclosure provides improved methods of gasification comprising: adding one or more carbonaceous materials, adding a molecular oxygen-containing gas, adding a methane-containing gas and optionally adding water or steam into said gasifier. This disclosure is also directed to process of production of one or more alcohols from said syngas via fermentation or digestion in the presence of at least one microorganism.

17 Claims, 6 Drawing Sheets

(56) References Cited

U.S. PATENT DOCUMENTS

| | | |
|---|---|---|
| 2008/0210089 A1 | 9/2008 | Tsangaris et al. |
| 2008/0244976 A1 | 10/2008 | Paisley |
| 2008/0280236 A1 | 11/2008 | Wright |
| 2009/0018221 A1 | 1/2009 | Klepper et al. |
| 2009/0018222 A1 | 1/2009 | Klepper et al. |
| 2009/0090053 A1 | 4/2009 | Feldmann |
| 2009/0156695 A1 | 6/2009 | Young |
| 2009/0235587 A1* | 9/2009 | Hawkes et al. ............ 48/202 |
| 2009/0293359 A1* | 12/2009 | Simmons et al. ............ 48/127.7 |
| 2010/0256246 A1 | 10/2010 | Carryer et al. |
| 2010/0280137 A1* | 11/2010 | Kukkonen et al. ............ 518/712 |
| 2010/0317077 A1* | 12/2010 | Gaddy et al. ............ 435/161 |
| 2010/0330640 A1* | 12/2010 | Bell et al. ............ 435/162 |
| 2011/0248218 A1 | 10/2011 | Sutradhar et al. |
| 2011/0250662 A1 | 10/2011 | Sutradhar et al. |

FOREIGN PATENT DOCUMENTS

| | | |
|---|---|---|
| WO | 2007/117157 | 10/2007 |
| WO | 2007/131241 | 11/2007 |
| WO | 2008/098311 | 8/2008 |
| WO | WO 2009/022925 | 2/2009 |
| WO | WO 2009/064200 | 5/2009 |
| WO | 2009/076138 | 6/2009 |
| WO | 2009/112334 | 9/2009 |
| WO | 2009/154788 | 12/2009 |

* cited by examiner

US 8,999,021 B2

METHODS FOR GASIFICATION OF CARBONACEOUS MATERIALS

FIELD

The present disclosure is generally directed to process of gasification of carbonaceous materials to produce synthesis gas or syngas. This disclosure is directed to method of co-gasification of a methane-containing gas such as landfill gas with carbonaceous material to produce syngas. This disclosure is also directed to process of production of one or more alcohols from said syngas via fermentation or digestion in the presence of at least one microorganism.

BACKGROUND

The present disclosure contemplates production of synthesis gas comprising CO, $CO_2$, and $H_2$ via gasification of carbonaceous materials. Synthesis gas can be used to produce one or more chemicals through biological or chemical routes. Synthesis gas can also be used to produce energy to generate electricity.

Thus syngas can be acted upon by fermentation or digestion by certain microorganisms to produce alcohols (methanol, ethanol, propanol, butanol, etc.), acetic acid, acetates, hydrogen, etc. Various strains of acetogens have been described for use in the production of liquid fuels from syngas: *Butyribacterium methylotrophicum, Clostridium autoethanogenum, Clostridium carboxidivorans, Clostridium ljungdahlii, Clostridium ragsdalei*.

U.S. Pat. No. 5,173,429 to Gaddy et al. discloses *Clostridium ljungdahlii* ATCC No. 49587, an anaerobic microorganism that produces ethanol and acetate from synthesis gas. U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380. U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989. U.S. Pat. No. 6,136,577 to Gaddy et al. discloses a method and apparatus for converting waste gases into useful products such as organic acids and alcohols (particularly acetic acid) using anaerobic strains of *Clostridium ljungdahlii*. U.S. Pat. No. 6,753,170 to Gaddy et al. discloses an anaerobic microbial fermentation process for the production of acetic acid. U.S. Pat. No. 7,285,402 to Gaddy et al. discloses an anaerobic microbial fermentation process for the production of alcohol.

US Patent Application No. 20070275447 discloses a clostridia bacterial species (*Clostridium carboxidivorans*, ATCC BAA-624, "P7") that is capable of synthesizing, from waste gases, products which are useful as biofuel. US Pat. Appl. No. 20080057554 discloses a clostridia bacterial species (*Clostridium ragsdalei*, ATCC BAA-622, "P11") that is capable of synthesizing, from waste gases, products which are useful as biofuel.

WO 2007/117157 discloses methods of anaerobic fermentation processes that produce acetate as a by-product in addition to a desired product, and that can utilize hydrogen and/or carbon dioxide in the fermentation. In this disclosure fermentation is carried out by one or more strains of bacteria selected from *Clostridium, Moorella* and *Carboxydothermus*. WO 2009/064200 discloses a class of bacteria which has improved efficiency in the production of ethanol by anaerobic fermentation of substrates containing carbon monoxide. As disclosed, the exemplified bacterium, *Clostridium autoethanogenum*, is capable of producing ethanol and acetate.

Syngas can be converted to various chemicals and fuels using chemical catalytic routes such as process using catalysts containing Cu & Zn to make methanol or mixed alcohols, process using catalysts containing Co & Rh to produce ethanol and Fischer-Tropsch type synthesis to make olefins, etc. WO 2009/035851 discloses methods of converting syngas into ethanol and/or other higher alcohols using reactors comprising catalyst capable of converting syngas to alcohols said catalyst comprising at least one Group IB element, at least one Group IIB element, and at least one Group IIIA element.

WO 2010/002618 discloses a method for making alcohols from a gas comprising hydrogen and carbon monoxide comprising: passing the gas through a reactor containing a carried catalyst comprising elemental molybdenum, cobalt and an alkali or alkaline earth metal, and/or hydrides thereof.

Production of chemicals or power in general depends upon the quality of syngas produced, e.g. amount or concentration of CO and $H_2$ in syngas as well as the ratio of $CO/H_2$. Methods known for increasing ethanol yield by improving concentration CO and $H_2$ in syngas as well as the ratio of $CO/H_2$ include co-gasification of carbon dioxide, methane-containing gas such as landfill gas with carbonaceous material in the gasifier. WO 2009/154788 discloses a method of synthesis gas production via gasification of carbonaceous material in a gasifier comprising: injecting carbon dioxide gas, oxygen gas, and carbonaceous material into a gasifier; creating syngas comprising carbon monoxide and hydrogen.

WO 2009/112334 discloses a process wherein there is fed to the gasification step of gasifiable feedstock landfill gas which is mixture of predominantly methane, carbon dioxide and hydrogen sulfide obtained at a landfill site.

Thus U.S. Pat. No. 6,595,001 disclose a method of utilizing a methane-containing gas by feeding the methane-containing gas to a gas engine/generator assembly.

A widely used process of gasification of carbonaceous materials to produce syngas rich in CO and $H_2$ uses an oxygen-deficient or oxygen-starved atmosphere in the gasifier that prevents complete conversion of carbon in the carbonaceous material. However, under oxygen-starved condition part of the carbon content of the carbonaceous materials often remains as un-reacted carbon particles or soot in the product syngas. Another part of the carbon content of the carbonaceous materials remains as un-reacted carbon in ash. Incomplete conversion of carbonaceous feedstock to CO and $H_2$ means less available CO and $H_2$ for production of power or chemicals (e.g. ethanol). Increased amount of un-reacted or unconverted carbon particles or soot in the raw syngas increases difficulty and cost of cleaning up syngas. Increased amount of un-reacted carbon in ash increases difficulty and cost of disposal of ash.

It would be desirable to have a method of operation of gasifier that maximizes production of power or chemicals from the syngas produced from gasifier while keeping amount of un-reacted or unconverted carbon particles or soot in the raw syngas and amount of un-reacted carbon in ash under desirable low values especially when a methane-containing gas is co-gasified with carbonaceous material feed.

The present disclosure provides various new and desirable gasifier designs and methods of operating a gasifier that are not known in the art. The present disclosure accomplishes the needs described above.

SUMMARY

The present disclosure provides for a method of gasification of carbonaceous materials in a gasifier to produce a product gas comprising carbon monoxide, carbon dioxide, hydrogen, and tar; said method comprising: adding one or more carbonaceous materials, adding a molecular oxygen-containing gas, adding a methane-containing gas and optionally adding water or steam into said gasifier; wherein amount of total oxygen added to said gasifier in pounds per pound of total carbon added to said gasifier comprises greater than about 0.75. In one embodiment amount of total oxygen added to said gasifier in pounds per pound of total carbon added to said gasifier comprises about 0.75 to about 3.0. In one embodiment said methane-containing gas comprises one or more gases selected from: alkanes, alkenes, alkynes, landfill gas, biogas, digester gas, and natural gas.

As an embodiment, the present disclosure further comprising treating said product gas at a temperature of about 1750° F. to about 3500° F. in the presence of molecular oxygen to produce a raw syngas comprising carbon monoxide, hydrogen, and syngas-carbon. In one embodiment raw syngas also comprises carbon dioxide.

The present disclosure provides a method of gasification of carbonaceous materials in a gasifier to produce syngas using partial oxidation method; said gasifier comprising a first reaction zone and a second reaction zone; said method comprising: adding one or more carbonaceous materials into said first reaction zone of gasifier; adding a molecular oxygen containing gas, a methane-containing gas and optionally adding water or steam into one or both of said first reaction zone and second reaction zone of said gasifier; wherein amount of total oxygen added to said gasifier in pounds per pound of total carbon added to said gasifier comprises greater than about 1.25. In one embodiment amount of total oxygen added into said first reaction zone of said gasifier in pounds per pound of total carbon added to said gasifier comprises about 1.25 to about 3.5.

The present disclosure provides a method of gasification of carbonaceous materials in a gasifier to produce syngas; said gasifier comprising a first reaction zone and a second reaction zone; said method comprising: adding one or more carbonaceous materials into said first reaction zone of gasifier; adding a molecular oxygen containing gas, a methane-containing gas and optionally adding water or steam into one or both of said first reaction zone and second reaction zone of said gasifier; wherein amount of total oxygen added to said gasifier in pounds per pound of total carbon added to said gasifier comprises greater than about 1.25. In one embodiment amount of total oxygen added into said first reaction zone of said gasifier in pounds per pound of total carbon added to said gasifier comprises about 1.25 to about 3.5.

As an embodiment the present disclosure provides a method further comprising: subjecting said raw syngas to cooling and cleaning up to produce a clean syngas; contacting said clean syngas with a biocatalyst in a fermentation container to produce an alcohol product mixture.

BRIEF DESCRIPTION OF THE FIGURES

FIG. 1 presents an embodiment of a two-stage gasification process.

DETAILED DESCRIPTION

Definitions

Figure 1:
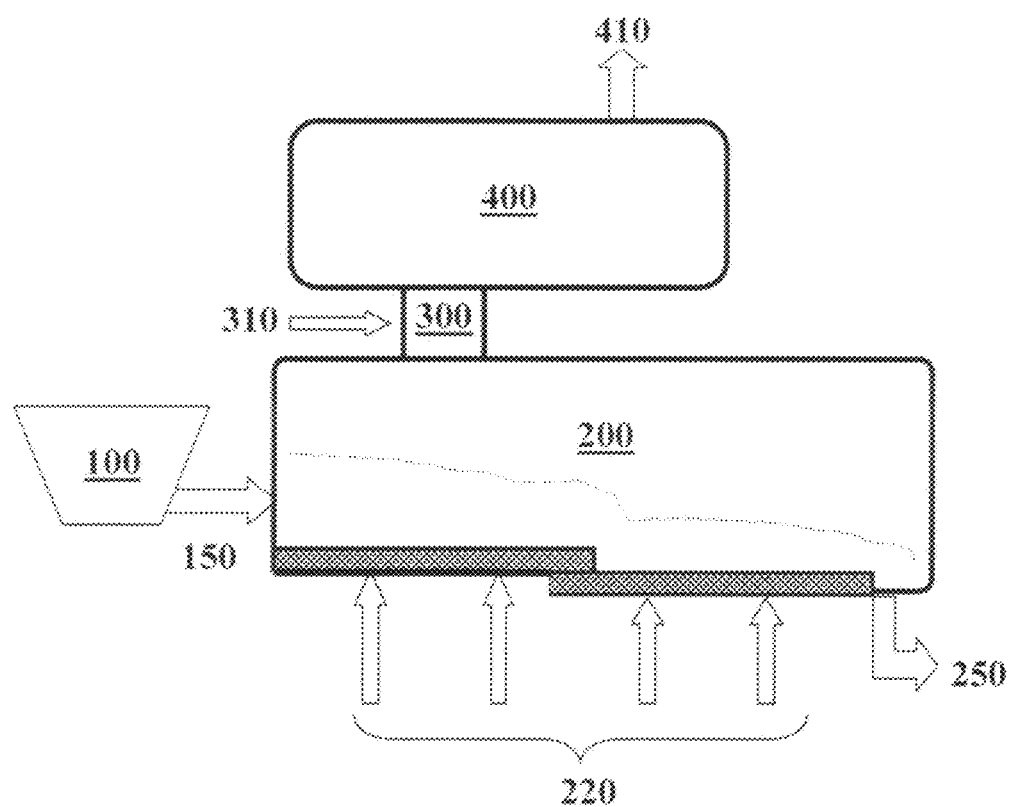
FIG. 1 comprises a schematic diagram illustrating an embodiment of the gasification process for this present disclosure.

Unless otherwise defined, the following terms as used throughout this specification for the present disclosure are defined as follows and can include either the singular or plural forms of definitions below defined:

The term "about" modifying any amount refers to the variation in that amount encountered in real world conditions, for example, the variation in that amount encountered in real world conditions of sustaining microorganism culture, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about."

The term "acetogen" or "acetogenic" refers to a bacterium that generates acetate as a product of anaerobic respiration. This process is different from acetate fermentation, although both occur in the absence of oxygen and produce acetate. These organisms are also referred to as acetogenic bacteria, since all known acetogens are bacteria. Acetogens are found in a variety of habitats, generally those that are anaerobic (lack oxygen). Acetogens can use a variety of compounds as sources of energy and carbon; the best studied form of acetogenic metabolism involves the use of carbon dioxide as a carbon source and hydrogen as an energy source.

The term "ash-carbon" or "Ash-carbon" or "Ash-Carbon" means content of unconverted carbon in ash removed from gasifier.

The term "ash fusion temperature" means temperature at which at least a portion of ash or inorganic matter contained in carbonaceous material melts. Typically this temperature comprises about 1400° F.

The term "biocatalyst" means, for the present disclosure, natural catalysts, protein enzymes, living cells, microorganisms, and bacteria.

The terms "bioreactor," "reactor," or "fermentation bioreactor," include a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact. Preferably for the method of this disclosure, the fermentation bioreactor comprises a growth reactor which feeds the fermentation broth to a second fermentation bioreactor, in which most of the product, ethanol, is produced.

"Carbonaceous material" as used herein refers to carbon rich material such as coal, and petrochemicals. However, in this specification, carbonaceous material includes any carbon material whether in solid, liquid, gas, or plasma state. Among the numerous items that can be considered carbonaceous material, the present disclosure contemplates: carbonaceous liquid product, carbonaceous industrial liquid recycle, carbonaceous municipal solid waste (MSW or msw), carbonaceous urban waste, carbonaceous agricultural material, carbonaceous forestry material, carbonaceous wood waste, carbonaceous construction material, carbonaceous vegetative material, carbonaceous industrial waste, carbonaceous fermentation waste, carbonaceous petrochemical coproducts, carbonaceous alcohol production coproducts, carbonaceous coal, tires, plastics, waste plastic, coke oven tar, fibersoft, lignin, black liquor, polymers, waste polymers, polyethylene terephthalate (PETA), polystyrene (PS), sewage sludge, animal waste, crop residues, energy crops, forest processing residues, wood processing residues, livestock wastes, poultry wastes, food processing residues, fermentative process wastes, ethanol coproducts, spent grain, spent microorganisms, or their combinations. For this disclosure carbon dioxide and methane-containing gas are not considered carbonaceous materials. For avoidance of doubt, various carbonaceous material(s) can be construed in either the singular or plural form, where appropriate, regardless of singular or plural form word usage as provided in this definition.

The term "fermentation" means fermentation of CO to alcohols and acetate. A number of anaerobic bacteria are known to be capable of carrying out the fermentation of CO to alcohols, including butanol and ethanol, and acetic acid, and are suitable for use in the process of the present disclosure. Examples of such bacteria that are suitable for use in the disclosure include those of the genus *Clostridium*, such as strains of *Clostridium ljungdahlii*, including those described in WO 2000/68407, EP 117309, U.S. Pat. Nos. 5,173,429, 5,593,886, and 6,368,819, WO 1998/00558 and WO 2002/08438, and *Clostridium autoethanogenum*. Other suitable bacteria include those of the genus *Moorella*, including *Moorella* sp HUC22-1, and those of the genus *Carboxydothermus*. The disclosures of each of these publications will be fully incorporated herein by reference. In addition, other acetogenic anaerobic bacteria may be selected for use in the process of the disclosure by a person of skill in the art. It will also be appreciated that a mixed culture of two or more bacteria may be used in the process of the present disclosure. One microorganism suitable for use in the present disclosure is *Clostridium autoethanogenum* that is available commercially from DSMZ and having the identifying characteristics of DSMZ deposit number DSMZ 10061. The fermentation may be carried out in any suitable bioreactor, such as a continuous stirred tank reactor (CTSR), a bubble column reactor (BCR) or a trickle bed reactor (TBR). Also, in some preferred embodiments of the disclosure, the bioreactor may comprise a first, growth reactor in which the microorganisms are cultured, and a second, fermentation reactor, to which fermentation broth from the growth reactor is fed and in which most of the fermentation product (ethanol and acetate) is produced.

The term "fibersoft" or "Fibersoft" or "fibrosoft" or "fibrousoft" means a type of carbonaceous material that is produced as a result of softening and concentration of various substances; in an example carbonaceous material is produced via steam autoclaving of various substances. In another example, the fibersoft can comprise steam autoclaving of municipal, industial, commercial, medical waste resulting in a fibrous mushy material.

"Gasifier" or "gasifier" means counter-current fixed bed gasifer, co-current fixed bed gasifier, moving bed, fluidized bed gasifier, entrained flow gasifier, plasma arc gasifier, single stage gasifier, multistage gasifier, two stage gasifier, three stage gasifer, four stage gasifer, five stage gasifer, and their combinations.

The term "microorganism" includes bacteria, fungi, yeast, archaea, and protists; microscopic plants (called green algae); and animals such as plankton, the planarian and the amoeba. Some also include viruses, but others consider these as non-living. Microorganisms live in all parts of the biosphere where there is liquid water, including soil, hot springs, on the ocean floor, high in the atmosphere and deep inside rocks within the Earth's crust. Microorganisms are critical to nutrient recycling in ecosystems as they act as decomposers. Microbes are also exploited by people in biotechnology, both in traditional food and beverage preparation, and in modern technologies based on genetic engineering. It is envisioned that mixed strain microorganisms, that may or may not contain strains of various microorganisms, will be utilized in the present disclosure. Also, it is envisioned that directed evolution can selectively screen microorganisms that can be utilized in the present disclosure. It is further envisioned that recombinant DNA technology can create microorganisms using select strains of existing microorganisms. It is envisioned that acetogenic anaerobic (or facultative) bacteria, which are able to convert CO and water or $H_2$ and $CO_2$ into ethanol and acetic acid products will be utilized in the present disclosure. Useful bacteria according to this disclosure include, without limitation, *Acetogenium kivui, Acetobacterium woodii, Acetoanaerobium noterae, Butyribacterium methylotrophicum, Caldanaerobacter subterraneus, Caldanaerobacter subterraneus pacificus, Carboxydothermus hydrogenoformans, Clostridium aceticum, Clostridium. acetobutylicum, Clostridium Autoethanogenum, Clostridium thermoaceticum, Eubacterium limosum, Clostridium ljungdahlii* PETC, *Clostridium ljungdahlii* ER12, *Clostridium ljungdahlii* C-01, *Clostridium ljungdahlii* O-52, *Clostridium ultunense, Clostridium ragsdalei, Clostridium carboxidivorans, Geobacter sulfurreducens, Moorella, Moorella thermacetica*, and *Peptostreptococcus productus*. Other acetogenic anaerobic bacteria are selected for use in these methods by one of skill in the art. In some embodiments of the present disclosure, several exemplary strains of *C. ljungdahlii* include strain PETC (U.S. Pat. No. 5,173,429); strain ER12 (U.S. Pat. No. 5,593,886) and strains C-01 and O-52 (U.S. Pat. No. 6,136,577). These strains are each deposited in the American Type Culture Collection, 10801 University Boulevard, Manassas, Va. 20110-2209, under Accession Nos.: 55383 (formerly ATCC No. 49587), 55380, 55988, and 55989 respectively. Each of the strains of *C. ljungdahlii* is an anaerobic, gram-positive bacterium with a guanine and cytosine (G+C) nucleotide content of about 22 mole %. These bacteria use a variety of substrates for growth, but not methanol or lactate. These strains differ in their CO tolerance, specific gas uptake rates and specific productivities. In the "wild" strains found in nature, very little ethanol production is noted. Strains of *C. ljungdahlii* operate ideally at 37.degree. C., and typically produce an ethanol to acetyl (i.e. which refers to both free or molecular acetic acid and acetate salts) product ratio of about 1:20 (1 part ethanol per 20 parts acetyl) in the "wild" state. Ethanol concentrations are typically only 1-2 g/L. While this ability to produce ethanol is of interest, because of low ethanol productivity the "wild" bacteria cannot be used to economically produce ethanol on a commercial basis. With minor nutrient manipulation the above-mentioned *C. ljungdahlii* strains have been used to produce ethanol and acetyl with a product ratio of 1:1 (equal parts ethanol and acetyl), but the ethanol concentration is less than 10 g/L, a level that results in low productivity, below 10 g/L-day. In addition culture stability is an issue, primarily due to the relatively high (8-10 g/L) concentration of acetyl (2.5-3 g/L molecular acetic acid) in combination with the presence of ethanol. Furthermore, as the gas rate is increased in an effort to produce more ethanol, the culture is inhibited, first by molecular acetic acid and then by CO. As a result, the culture becomes unstable and fails to uptake gas and produce additional product. Further, early work by the inventors showed difficulty in producing more than a 2:1 ratio of ethanol to acetyl in a steady state operation. A large number of documents describe the use of anaerobic bacteria, other than *C. ljungdahlii*, in the fermentation of sugars that do not consume CO, $CO_2$ and $H_2$ to produce solvents. In an attempt to provide high yields of ethanol, a variety of parameters have been altered which include: nutrient types, microorganism, specific addition of reducing agents, pH variations, and the addition of exogenous gases.

The term "municipal solid waste" or "MSW" or "msw" means waste comprising household, commercial, industrial and/or residual waste.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is also used as an intermediate in producing synthetic petroleum for use as a fuel or lubricant via Fischer-Tropsch synthesis and previously the Mobil methanol to gasoline process. Syngas consists primarily of hydrogen, carbon monoxide, and very often some carbon dioxide, and has less than half the energy density (i.e., BTU content) of natural gas. Syngas is combustible and often used as a fuel source or as an intermediate for the production of other chemicals.

The term "syngas-carbon" or "Syngas-carbon" or "Syngas-Carbon" means content of unconverted carbon particles in raw syngas produced from gasification process.

The term "total carbon input into gasifier" or "total carbon added into gasifier" means sum of all carbon contained in anything fed into the gasifier, e.g. carbon contained in one or more carbonaceous materials as defined above, and carbon contained in methane-containing gas added into the gasifier.

The term "total carbon input into first reaction zone of gasifier" or "total carbon added into first reaction zone of gasifier" means sum of all carbon contained in anything fed into first reaction zone of the gasifier, e.g. carbon contained in one or more carbonaceous materials as defined above, and carbon contained in methane-containing gas added into first reaction zone of the gasifier.

The term "total oxygen input into gasifier" or "total oxygen added into gasifier" means sum of all oxygen contained in anything fed into the gasifier, e.g. oxygen contained in one or more carbonaceous materials as defined above, oxygen contained in hydrocarbon containing gas added into the gasifier, oxygen contained in any water or steam optionally added into the gasifier and oxygen contained in molecular oxygen containing gas added into the gasifier (in both the first reaction zone and the second reaction zone).

The term "total oxygen input into first reaction zone of gasifier" or "total oxygen added into first reaction zone of gasifier" means sum of all oxygen contained in anything fed into first reaction zone of the gasifier, e.g. oxygen contained in one or more carbonaceous materials as defined above added into the first reaction zone of the gasifier, oxygen contained in methane-containing gas added into first reaction zone of the gasifier, oxygen contained in any water or steam added into first reaction zone of the gasifier and oxygen contained in molecular oxygen containing gas added into the first reaction zone of the gasifier.

DETAILED DESCRIPTION

The present disclosure will now be described more fully and with reference to the figures in which various embodiments of the present disclosure are shown. The subject matter of this disclosure may, however, be embodied in many different forms and should not be construed as being limited to the embodiments set forth herein.

The present disclosure provides a method of gasification of carbonaceous materials in a gasifier to produce a product gas comprising carbon monoxide, carbon dioxide, hydrogen, and tar; said method comprising: adding one or more carbonaceous materials, adding a molecular oxygen-containing gas, adding a methane-containing gas and optionally adding water or steam into said gasifier; wherein amount of total oxygen added to said gasifier in pounds per pound of total carbon added to said gasifier comprises greater than about 0.75. In one embodiment amount of total oxygen added to said gasifier in pounds per pound of total carbon added to said gasifier comprises about 0.75 to about 3.0. In one embodiment said methane-containing gas comprises one or more gases selected from: alkanes, alkenes, alkynes, landfill gas, biogas, digester gas, and natural gas.

As an embodiment, the present disclosure provides one or more said carbonaceous materials comprises selection from carbonaceous material, carbonaceous liquid product, industrial carbonaceous liquid recycle, carbonaceous municipal solid waste (MSW), carbonaceous urban waste, carbonaceous agricultural material, carbonaceous forestry material, carbonaceous wood waste, carbonaceous construction material, carbonaceous vegetative material, carbonaceous petrochemical coproducts, carbonaceous coal, plastic, waste plastic, coke oven tar, fibersoft, tires, lignin, black liquor, polymers, waste polymers, polyethylene terephthalate (PETA), polystyrene (PS), sewage sludge, animal waste, crop residues, energy crops, forest processing waste, wood processing residues, livestock waste, poultry wastes, food processing residues, fermentative process wastes, carbonaceous industrial waste, alcohol production wastes, ethanol coproducts, spent grains, spent microorganisms or their combinations. In one embodiment carbon content of one or more said carbonaceous materials comprises about 0.25 to about 1.0 pound per pound of one or more said carbonaceous materials on a water free basis. In one embodiment hydrogen content of one or more said carbonaceous materials comprises about 0.0 to about 0.25 pound per pound of one or more said carbonaceous materials on a water free basis. In one embodiment oxygen content of one or more said carbonaceous materials comprises about 0.0 to about 0.5 pound per pound of one or more said carbonaceous materials on a water free basis. In one embodiment, said carbonaceous material comprises a plurality of carbonaceous materials selected from carbonaceous material, carbonaceous liquid product, industrial carbonaceous liquid recycle, carbonaceous municipal solid waste (MSW), carbonaceous urban waste, carbonaceous agricultural material, carbonaceous forestry material, carbonaceous wood waste, carbonaceous construction material, carbonaceous vegetative material, carbonaceous petrochemical coproducts, carbonaceous coal, plastic, waste plastic, coke oven tar, fibersoft, tires, lignin, black liquor, polymers, waste polymers, polyethylene terephthalate (PETA), polystyrene (PS), sewage sludge, animal waste, crop residues, energy crops, forest processing residues, wood processing residues, livestock wastes, poultry wastes, food processing residues, fermentative process wastes, carbonaceous industrial waste, alcohol production wastes, ethanol coproducts, spent grains, spent microorganisms or combinations of any of these.

As an embodiment, the gasifier produces ash comprising ash-carbon and wherein said ash comprises less than about 5% of ash-carbon.

As an embodiment, the present disclosure comprises treating said product gas at a temperature of about 1750° F. to about 3500° F. in the presence of molecular oxygen to produce a raw syngas comprising carbon monoxide, hydrogen, and syngas-carbon. In one embodiment raw syngas also comprises carbon dioxide.

As an embodiment, said raw-syngas comprises less than about 0.5 pound syngas-carbon per 1000 SCF raw-syngas produced.

As an embodiment, carbon to hydrogen mass ratio in one or more of said carbonaceous material comprises 1 to 20.

As an embodiment, carbon to oxygen mass ratio in one or more of said carbonaceous material comprises 1 to 200.

The present disclosure provides a method of gasification of carbonaceous materials in a gasifier to produce syngas using partial oxidation method; said gasifier comprising a first reaction zone and a second reaction zone; said method comprising: adding one or more carbonaceous materials into said first reaction zone of gasifier; adding a molecular oxygen containing gas, a methane-containing gas and optionally adding water or steam into one or both of said first reaction zone and second reaction zone of said gasifier; wherein amount of total oxygen added to said gasifier in pounds per pound of total carbon added to said gasifier comprises greater than about 1.25. In one embodiment amount of total oxygen added into said first reaction zone of said gasifier in pounds per pound of total carbon added to said gasifier comprises about 1.25 to about 3.5. In one embodiment said first reaction zone temperature comprises 650-1450° F. In one embodiment said second reaction zone temperature comprises 1750-3500° F. As an embodiment the present disclosure comprises adding methane-containing gas in the first reaction zone of said gasifier.

The present disclosure provides a method of gasification of carbonaceous materials in a gasifier to produce syngas; said gasifier comprising a first reaction zone and a second reaction zone; said method comprising: adding one or more carbonaceous materials into said first reaction zone of gasifier; adding a molecular oxygen containing gas, a methane-containing gas and optionally adding water or steam into one or both of said first reaction zone and second reaction zone of said gasifier; wherein amount of total oxygen added to said gasifier in pounds per pound of total carbon added to said gasifier comprises greater than about 1.25. In one embodiment amount of total oxygen added into said first reaction zone of said gasifier in pounds per pound of total carbon added to said gasifier comprises about 1.25 to about 3.5. In one embodiment said first reaction zone temperature comprises 650-1450° F. In one embodiment said second reaction zone temperature comprises 1750-3500° F. As an embodiment the present disclosure comprises adding methane-containing gas in the first reaction zone of said gasifier.

As an embodiment the present disclosure comprises: subjecting said raw syngas to cooling and cleaning up to produce a clean syngas; contacting said clean syngas with a biocatalyst in a fermentation container to produce an alcohol product mixture.

The methane-containing gas comprises one or more gases selected from: methane, propane, landfill gas, biogas, digester gas, and natural gas. In one embodiment of the present disclosure, said methane-containing gas comprises methane. In one embodiment, said methane-containing gas comprises propane. In one embodiment, said methane-containing gas comprises landfill gas. In one embodiment, said methane-containing gas comprises digester gas. In one embodiment, said methane-containing gas comprises natural gas. In one embodiment, said methane-containing gas comprises biogas.

In one embodiment of this disclosure the temperature of said gasifier comprises about 650° F. to about 3500° F. In one embodiment the temperature comprises about 650° F. to about 1450° F. In one embodiment the temperature of said gasifier comprises about 950° F. to about 1400° F. In one embodiment the temperature of said gasifier is about 1400° F. In one embodiment the temperature of said gasifier comprises about 1750° F. to about 2250° F. In one embodiment the temperature of said gasifier is about 2250° F.

In various embodiments of the present disclosure said tar-containing product gas can be treated to remove or destroy at least a part of tar contained in said tar-containing product gas using various tar removal methods described in the published art in order to produce a tar-free or less tar-containing raw syngas. In one embodiment of the present disclosure said tar-containing product gas is treated at a temperature of about 1750° F. to about 3500° F. in the presence of molecular oxygen to remove or produce a raw syngas comprising carbon monoxide, hydrogen, and syngas-carbon. Presumably in such treatment tar is destroyed through cracking of tar. Presumably in such treatment tar is destroyed through partial oxidation of tar. In one embodiment the treatment temperature comprises about 1750° F. to about 2250° F. In one embodiment the treatment temperature is about 2250° F.

Operation of gasifier as above does not accomplish complete combustion of all carbon introduced in the gasifier to produce carbon dioxide. Presumably a partial oxidation of carbon is accomplished that increases production of carbon monoxide. Such partial oxidation may also lead to formation of un-reacted carbon particles or soot ("syngas-carbon") that remains in the raw syngas. Raw syngas containing large amount of syngas-carbon is undesirable as it increases difficulty and cost of cleaning raw syngas. In the method of this disclosure said raw-syngas comprises less than about 0.5 pound syngas-carbon per 1000 SCF raw-syngas produced. In one embodiment of the disclosure, said raw syngas comprises less than about 0.25 pound syngas-carbon per 1000 SCF raw syngas produced. In one embodiment, said raw syngas comprises less than about 0.125 pound syngas-carbon per 1000 SCF raw syngas produced.

Operation of gasifier as above does not accomplish complete combustion of all carbon introduced in the gasifier to produce carbon dioxide. Presumably incomplete oxidation of carbon is accomplished that increases production of carbon monoxide. Such incomplete oxidation may also lead to formation of un-reacted carbon particles or soot ("syngas-carbon") that remains in the raw syngas. Raw syngas containing large amount of syngas-carbon is undesirable as it increases difficulty and cost of cleaning raw syngas. In the method of this disclosure said raw-syngas comprises less than about 0.5 pound syngas-carbon per 1000 SCF raw-syngas produced. In one embodiment of the disclosure, said raw syngas comprises less than about 0.25 pound syngas-carbon per 1000 SCF raw syngas produced. In one embodiment, said raw syngas comprises less than about 0.125 pound syngas-carbon per 1000 SCF raw syngas produced.

Gasification of carbonaceous materials to produce tar-containing product gas and subsequent treatment of said tar-containing product gas at high temperature in the presence of molecular oxygen containing gas ("partial oxidation of tar") to produce tar-free or less-tar-containing raw syngas can be accomplished in multiple and separate process units or in a single unit with multiple reaction zones or chambers or compartments.

Gasification of carbonaceous materials to produce tar-containing product gas and subsequent treatment of said tar-containing product gas at high temperature in the presence of molecular oxygen containing gas ("tar cracking") to produce tar-free or less-tar-containing raw syngas can be accomplished in multiple and separate process units or in a single unit with multiple reaction zones or chambers or compartments.

In one embodiment of the instant disclosure, a gasification unit is used that comprises two reaction zones: a first reaction zone that produces a tar-containing product gas and a second reaction zone that produces tar-free or less-tar-containing raw syngas from tar-containing product gas.

In one embodiment of the instant disclosure, a multi-stage gasification unit is used that comprises two reaction zones: a first reaction zone that produces a tar-containing product gas and a second reaction zone that produces tar-free or less-tar-containing raw syngas from tar-containing product gas.

In one embodiment of the instant disclosure, a two-stage gasification unit is used that comprises two reaction zones: a first reaction zone that produces a tar-containing product gas and a second reaction zone that produces tar-free or less-tar-containing raw syngas from tar-containing product gas.

Temperature in the first reaction zone should not be above the melting point of the inorganic components of the carbonaceous materials that form ash. This temperature might be called ash-fusion temperature. In one embodiment, the first reaction zone is maintained at a temperature of about 650° F. to about 1450° F. In one embodiment, the first reaction zone is maintained at a temperature of about 950° F. to about 1450° F. In one embodiment, the first reaction zone is maintained at a temperature of about 1400° F.

Temperature in the second reaction zone should be high enough for tar-cracking and/or partial oxidation to occur effectively. In one embodiment, the second reaction zone is maintained at a temperature of about 1750° F. to about 3500° F. In one embodiment, the second reaction zone is maintained at a temperature of about 1750° F. to about 2250° F. In one embodiment, the second reaction zone is maintained at a temperature of about 2250° F. In addition to maintaining appropriate temperature, the second reaction zone should be sized in a way that an appropriate contact time or residence time is provided for tar-cracking and/or partial oxidation. Typically a residence time of about 2 to about 5 seconds is maintained.

In one embodiment, the second reaction zone is placed vertically above the first reaction zone. In one embodiment, the second reaction zone is placed vertically below the first reaction zone.

Molecular oxygen containing gas is added in the first reaction zone of said gasifier. Molecular oxygen containing gas is added in the second reaction zone of said gasifier. Molecular oxygen containing gas is added in both the first and the second reaction zones of said gasifier. Molecular oxygen containing gas can be air, oxygen-enriched air or pure oxygen. Molecular oxygen containing gas may contain from about 21 volume % to about 100 volume % molecular oxygen.

The methane-containing gas can be added in the first reaction zone of said gasifier. The methane-containing gas can be added in the second reaction zone of said gasifier. The methane-containing gas can be added simultaneously in both the first reaction zone and the second reaction zone of said gasifier.

In one embodiment of the disclosure, water is added to said gasifier. In one embodiment, at least a portion of water added to said gasifier is added as moisture present in said carbonaceous material. In one embodiment, at least a portion of water added to said gasifier is added by injecting steam directly into said gasifier. In one embodiment, at least a portion of water added to said gasifier is added by injecting steam directly into the first reaction zone of said gasifier.

In this disclosure, total oxygen is the sum of oxygen content of one or more carbonaceous materials added into gasifier, oxygen contained in any optionally added water or steam into gasifier, oxygen contained in methane-containing gas added into gasifier and molecular oxygen injected in both the first reaction zone or lower chamber and the second reaction zone or upper chamber of gasifier as oxygen containing gas; total carbon added in gasifier is the sum of carbon content of one or more carbonaceous materials added into gasifier and carbon contained in methane-containing gas added into gasifier.

In this disclosure, total oxygen added in first reaction zone is the sum of oxygen content of one or more carbonaceous materials added into first reaction zone of gasifier, oxygen contained in any optionally added water or steam added into first reaction zone of gasifier, oxygen contained in methane-containing gas added into first reaction zone of gasifier and oxygen contained in molecular oxygen containing gas added into first reaction zone of gasifier; total carbon added in first reaction zone of gasifier is the sum of carbon content of one or more carbonaceous materials added into first reaction zone of gasifier and carbon added through methane-containing gas added into first reaction zone of gasifier.

In one embodiment total carbon added in first reaction zone of gasifier is equal to total carbon added in gasifier.

In one embodiment total carbon added in first reaction zone of gasifier is not equal to total carbon added in gasifier.

In one embodiment, one or more said alcohols comprises methanol. In one embodiment, one or more said alcohols comprises ethanol. In one embodiment, one or more said alcohols comprises methanol, ethanol, propanol, butanol, and their combinations.

In one embodiment an alcohol is selectively recovered from the alcohol product mixture. In one embodiment, the alcohol selectively recovered is ethanol. In one embodiment, the alcohol selectively recovered is butanol.

As an embodiment, said biocatalyst comprises: microorganisms; acetogenic bacteria; one or more strains selected from *Clostridium, Moorella*, and *Carboxydothermus* or their mixed strains; *Clostridium ljungdahlii*. Said *Clostridium ljungdahlii* of the present disclosure is selected from the strains consisting of PETC, ERI-2, O-52 and C-01 or their combinations.

FIG. 1 comprises a schematic diagram illustrating an embodiment of a gasifier. FIG. 1 presents a schematic diagram of a two-stage gasifier. As an embodiment, FIG. 1 presents a schematic diagram of a two-stage gasifier using partial oxidation. Referring now to FIG. 1, one or more carbonaceous materials (150) is fed from a feed hopper (100) to the first reaction zone or lower chamber (200) of the gasifier for gasification. Molecular oxygen containing gas (220) is introduced into the lower chamber for assisting gasification. In one embodiment, water or steam can be added in the lower chamber to assist gasification. Amount of oxygen injected in the lower chamber is regulated in a way to prevent complete combustion of the carbonaceous material. In other words, the lower chamber is oxygen-starved. Prevention of complete combustion is also regulated by adjusting temperature in the lower chamber. A temperature in the range of 750 to 1450 degrees F. is maintained in the lower chamber. In one embodiment, the temperature in the lower chamber is adjusted in a way to prevent melting of any ash formed during gasification. In one embodiment, the temperature in the lower chamber is 1400 degrees F. In one embodiment, amount of molecular oxygen introduced in the lower chamber comprises is in the range of 10 to 100 pound-moles per ton of carbonaceous material on a dry or water free basis.

A stream of gaseous material produced in the first reaction zone or lower chamber moves to the second reaction zone or upper chamber (400) of the gasifier via the chamber (300) connecting the first reaction zone/lower chamber to the second reaction zone/upper chamber. A stream of ash (250) is removed from the lower chamber. A stream of gaseous material produced in the first reaction zone moves to the second reaction zone (400) of the gasifier via the connecting chamber (300) of the gasifier connecting the first reaction zone to the second reaction zone. A stream of ash (250) is removed from the first reaction zone.

Methane-containing gas can be added in first reaction zone/lower chamber (200). Methane-containing gas can be added in second reaction zone/upper chamber (400). Methane-containing gas can be added in first reaction zone/lower chamber (200) and second reaction zone/upper chamber (400). Methane-containing gas can be added in chamber connecting first reaction zone/lower chamber to second reaction zone/upper chamber. Methane-containing gas can be added in gas stream (310) going to chamber connecting first reaction zone/lower chamber to second reaction zone/upper chamber.

In an embodiment, steam can be added in first reaction zone/lower chamber (200). In an embodiment, steam can be added in second reaction zone/upper chamber (400). In an embodiment, steam can be added in first reaction zone/lower chamber (200) and second reaction zone/upper chamber (400). In an embodiment, steam can be added in chamber connecting first reaction zone/lower chamber to second reaction zone/upper chamber. In an embodiment, steam can be added in gas stream (310) going to chamber connecting first reaction zone/lower chamber to second reaction zone/upper chamber.

In an embodiment, continuous steam can be added in first reaction zone/lower chamber (200). In an embodiment, continuous steam can be added in second reaction zone/upper chamber (400). In an embodiment, continuous steam can be added in first reaction zone/lower chamber (200) and second reaction zone/upper chamber (400). In an embodiment, continuous steam can be added in chamber connecting first reaction zone/lower chamber to second reaction zone/upper chamber. In an embodiment, continuous steam can be added in gas stream (310) going to chamber connecting first reaction zone/lower chamber to second reaction zone/upper chamber.

Presumably, partial oxidation contained in the gaseous material produced in the lower chamber is accomplished in the upper chamber. Presumably, cracking of tar contained in the gaseous material produced in the lower chamber is accomplished in the upper chamber. A stream of oxygen containing gas in introduced in the chamber connecting first reaction zone/lower chamber to second reaction zone/upper chamber or throat of gasifier in order to assist the partial combustion in the upper chamber. A stream of oxygen containing gas in introduced in the chamber connecting first reaction zone/lower chamber to second reaction zone/upper chamber or throat of gasifier in order to assist cracking of tar in the upper chamber. In one embodiment, oxygen is introduced directly inside the upper chamber. Partial combustion is also regulated by adjusting the temperature in the upper chamber of gasifier. Cracking of tar is also regulated by adjusting the temperature in the upper chamber of gasifier. A temperature of 1750 to 3500 degrees F. is maintained in the upper chamber. In one embodiment, the temperature in the upper chamber is 2250 degrees F. In one embodiment, amount of molecular oxygen introduced in the upper chamber is in 10 to 100 pound-moles per ton of carbonaceous material on a dry or water free basis.

In one embodiment, the upper chamber is positioned at a level vertically above the top of the lower chamber. In one embodiment, the upper chamber is positioned at a level not vertically above the top of the lower chamber. In one embodiment, the lower chamber and upper chamber are positioned at about the same vertical elevation, i.e. side by side. A stream of raw syngas (410) is removed from the upper chamber of gasifier.

Figure 2:
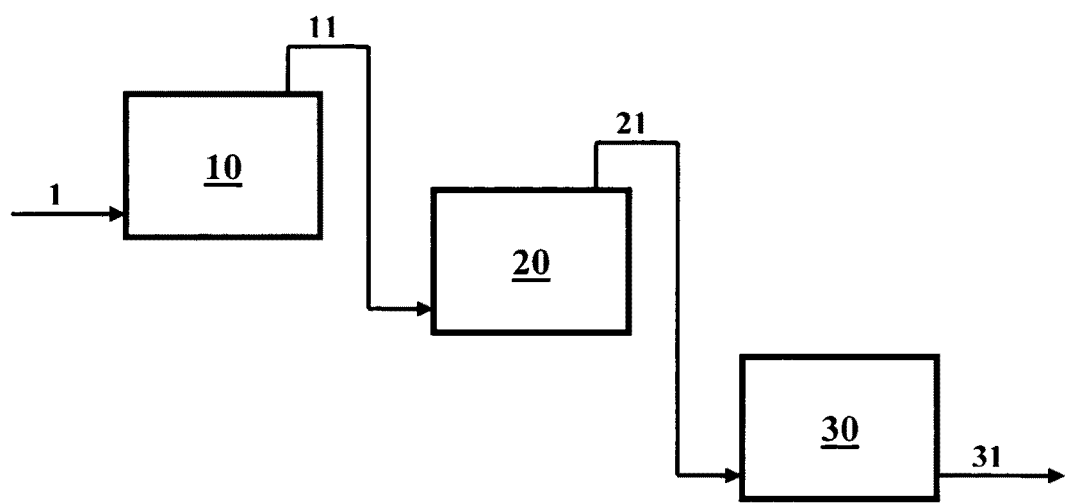
FIG. 2 comprises a schematic diagram illustrating an embodiment of the process of producing ethanol via gasification of carbonaceous materials.

FIG. 2 comprises a schematic diagram illustrating an embodiment of a process to produce ethanol from a carbonaceous material via gasification of said carbonaceous material. Referring now to FIG. 2, a carbonaceous material (1) is fed into a gasifier (10) wherein the carbonaceous material is converted to producer gas or synthesis gas or syngas comprising carbon monoxide (CO) and hydrogen ($H_2$). A raw syngas product (11) is removed from gasifier. The raw syngas is hot and it may contain sulfur-containing gas and other acidic gases, particulate material, etc and is subjected to cooling and clean up in a cooling and clean-up process (20). A cooled and cleaned up stream of syngas (21) is produced by the cooling and clean-up process that is introduced in a bioreactor or fermenter or fermentor (30) to produce ethanol. In the bioreactor carbon monoxide (CO) and hydrogen ($H_2$) of syngas is acted on by microorganisms to produce ethanol. An ethanol containing stream (31) is removed from the bioreactor. The ethanol containing stream can be further processed to produce fuel grade ethanol (not shown in diagram).

Figure 3:
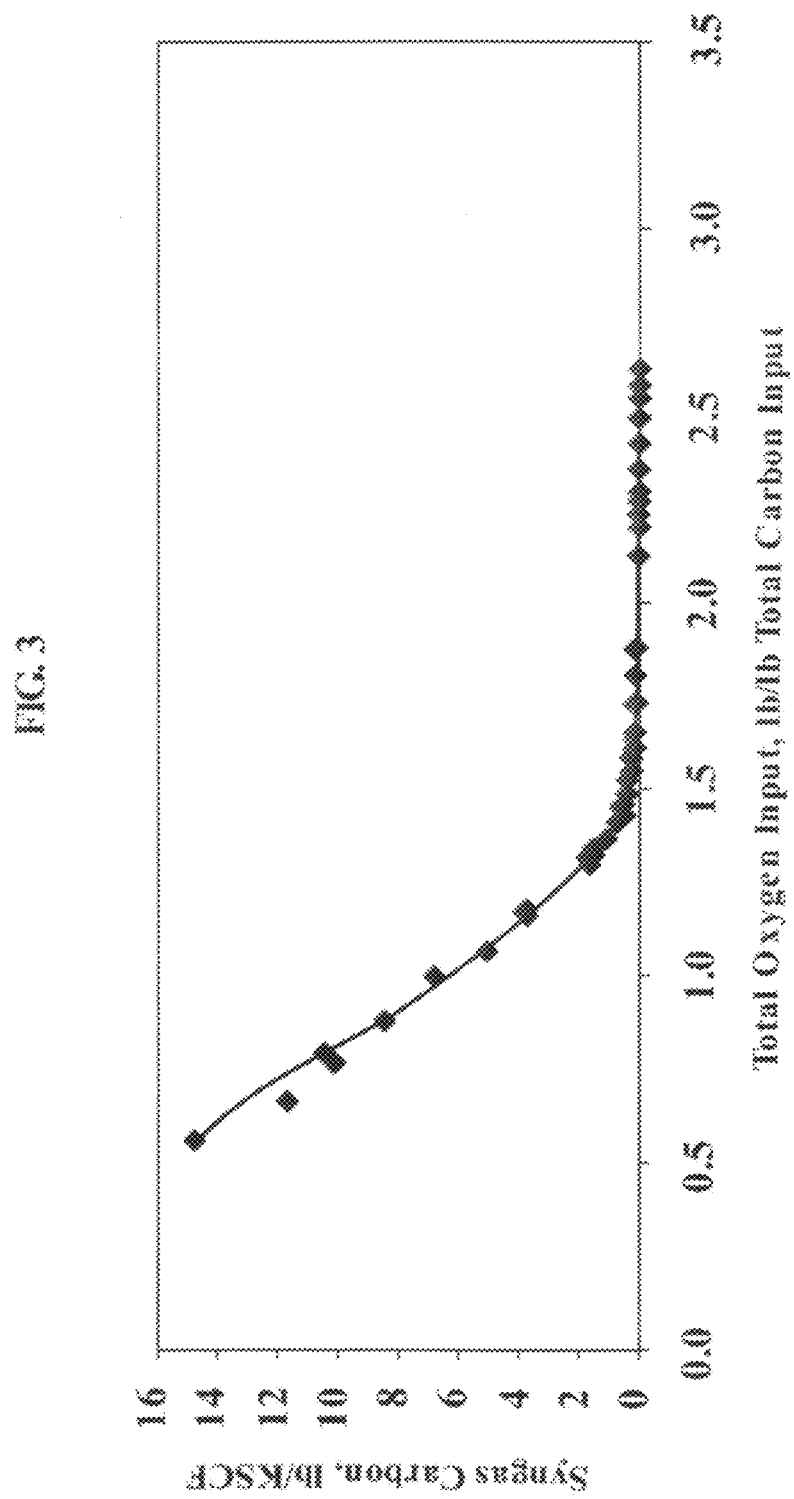
FIG. 3 comprises a schematic diagram illustrating an embodiment of the effect of total oxygen input into gasifier on syngas-carbon for various amounts of water input into gasifier.

FIG. 3 comprises a schematic diagram illustrating an embodiment of the effect of total oxygen input into gasifier on syngas-carbon for various amounts of water input into gasifier. As an embodiment, FIG. 3 illustrates that the trend of total syngas-carbon content decreases as the total oxygen input into gasifier increases. FIG. 3 is a plot of syngas carbon in pounds per KSCF of raw syngas produced (y-axis) versus total oxygen input in pounds per pound total carbon input (x-axis). FIG. 3 is a plot of syngas carbon in pounds per thousand SCF of raw syngas produced (y-axis) versus total oxygen input in pounds per pound total carbon input (x-axis). FIG. 3 is a plot of syngas carbon in pounds per thousand SCF of raw syngas produced (y-axis) versus total oxygen input in pounds per pound total carbon input (x-axis); wherein total oxygen input is total oxygen input into gasifier and total carbon input is total carbon input into gasifier. For a total oxygen input into gasifier greater than about 1.4 pound per pound (lb/lb) total carbon input into gasifier, raw syngas comprises less than about one (1) pound (lb) syngas-carbon per one thousand standard cubic feet (1000 SCF or KSCF) of raw syngas produced. For a total oxygen input into gasifier greater than about 1.5 pound per pound (lb/lb) total carbon input into gasifier, raw syngas comprises less than about 0.3 pound (lb) syngas-carbon per one thousand standard cubic feet (1000 SCF or KSCF) of raw syngas produced.

Figure 4:
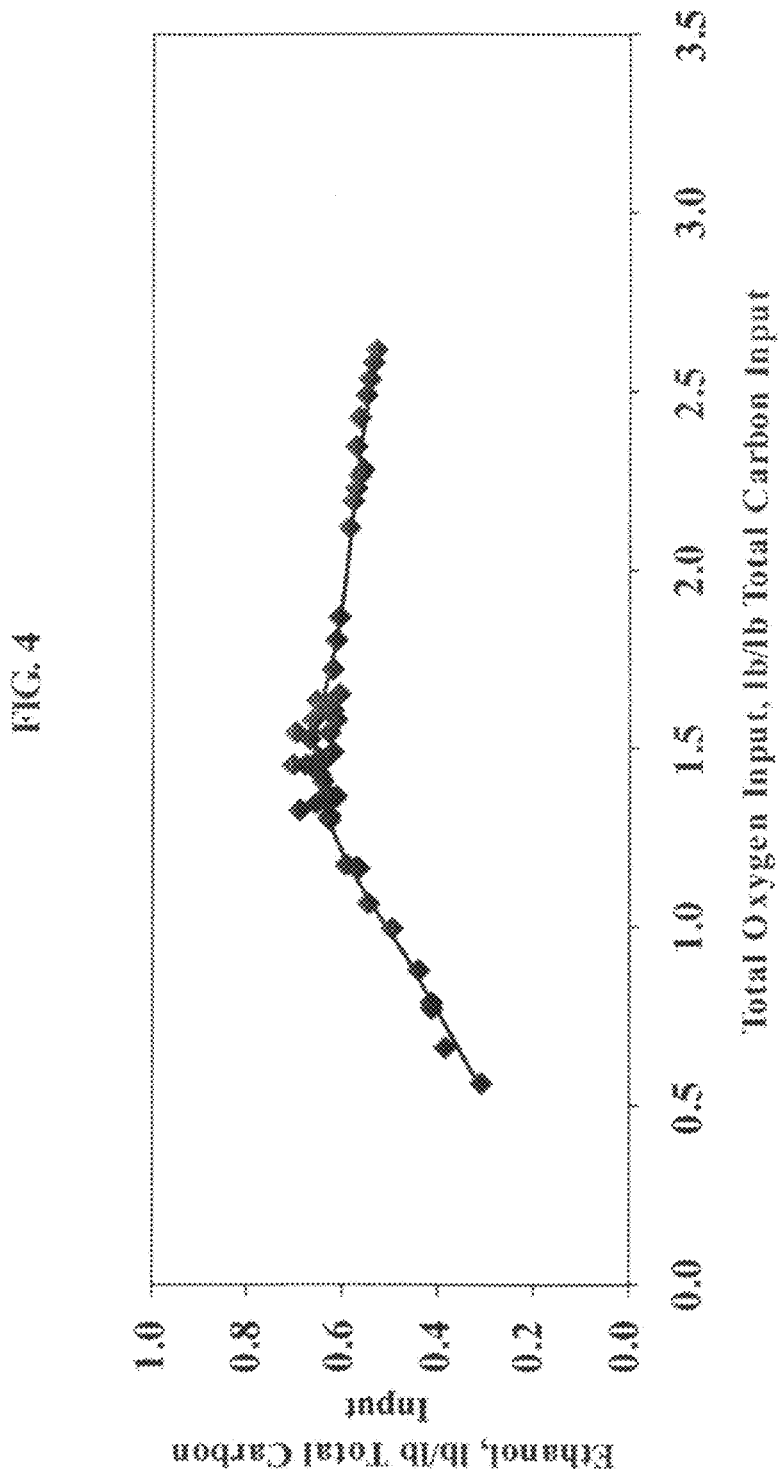
FIG. 4 comprises a schematic diagram illustrating an embodiment of the effect of total oxygen input into gasifier on amount of ethanol produced for various amounts of water input into gasifier.

FIG. 4 comprises a schematic diagram illustrating an embodiment of the effect of total oxygen input into gasifier on amount of ethanol produced for various amounts of water input into gasifier. As an embodiment, FIG. 4 illustrates that trend of the alcohol production trend initially increases with the increase in total oxygen input. FIG. 4 is a plot of ethanol produced in pounds per pound total carbon input (y-axis) versus total oxygen input in pounds per pound total carbon input (x-axis). FIG. 4 is a plot of ethanol produced in pounds per pound total carbon input (y-axis) versus total oxygen input in pounds per pound total carbon input (x-axis); wherein total oxygen input is total oxygen input into gasifier and total carbon input is total carbon input into gasifier. As an embodiment, FIG. 4 illustrates that trend of alcohol production initially increases with increase in total oxygen input and then decreases with increase in total oxygen input. As an embodiment, FIG. 4 illustrates that trend of ethanol production initially increases with increase in total oxygen input. As an embodiment, FIG. 4 illustrates that trend of ethanol production initially increases with the increase in total oxygen input and then decreases with increase in total oxygen input. As an embodiment, FIG. 4 illustrates that trend of ethanol production (pounds ethanol produced per pound of total carbon input into gasifier) increases with the increase in total oxygen input into gasifier up to total oxygen input of about one and a half (1.5) pound per pound (lb/lb) total carbon input into gasifier. As an embodiment, FIG. 4 illustrates that trend of ethanol production (pounds ethanol produced per pound of total carbon input into gasifier) increases with the increase in total oxygen input into gasifier up to total oxygen input of about one and a half (1.5) pound per pound (lb/lb) total carbon input into gasifier and above one and a half (1.5) pound total oxygen input per pound (lb/lb) total carbon input into gasifier, ethanol production (pounds ethanol produced per pound of total carbon input into gasifier) decreases with increase in total oxygen input into gasifier.

Figure 5:
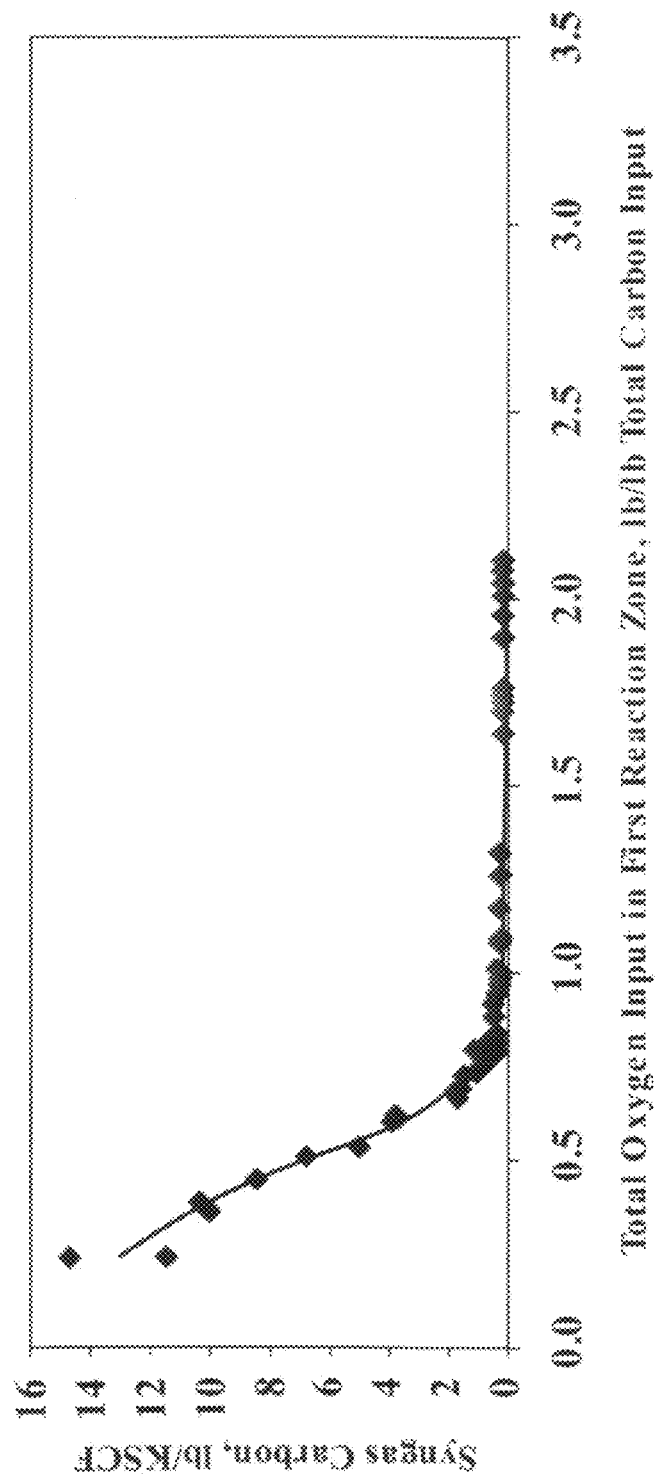
FIG. 5 comprises a schematic diagram illustrating an embodiment of the effect of total oxygen input into first reaction zone of gasifier on syngas-carbon for various amounts of water input into gasifier.

FIG. 5 comprises a schematic diagram illustrating an embodiment of the effect of total oxygen input into first reaction zone of gasifier on syngas-carbon for various amounts of water input into gasifier. As an embodiment, FIG. 5 illustrates that the trend of total syngas-carbon content of raw syngas decreases as the total oxygen input into first reaction zone of gasifier increases. FIG. 5 is a plot of syngas carbon in pounds per KSCF of raw syngas produced (y-axis) versus total oxygen input into first reaction zone in pounds per pound total carbon input (x-axis). FIG. 5 is a plot of syngas carbon in pounds per thousand SCF of raw syngas produced (y-axis) versus total oxygen input into first reaction zone in pounds per pound total carbon input (x-axis). FIG. 5 is a plot of syngas carbon in pounds per thousand SCF of raw syngas produced (y-axis) versus total oxygen input into first reaction zone in pounds per pound total carbon input (x-axis); wherein total oxygen input into first reaction zone is total oxygen input into first reaction zone of gasifier and total carbon input is total carbon input into gasifier. For a total oxygen input into the first reaction zone of gasifier greater than about 0.75 pound per pound (lb/lb) total carbon input into gasifier, raw syngas comprises less than about one (1) pound (lb) syngas-carbon per one thousand standard cubic feet (1000 SCF) of raw syngas produced. For a total oxygen input into first reaction zone of gasifier greater than about 0.9 pound per pound (lb/lb) total carbon input into gasifier, raw syngas comprises less than about 0.3 pound (lb) syngas-carbon per one thousand standard cubic feet (1000 SCF or KSCF) of raw syngas produced.

Figure 6:
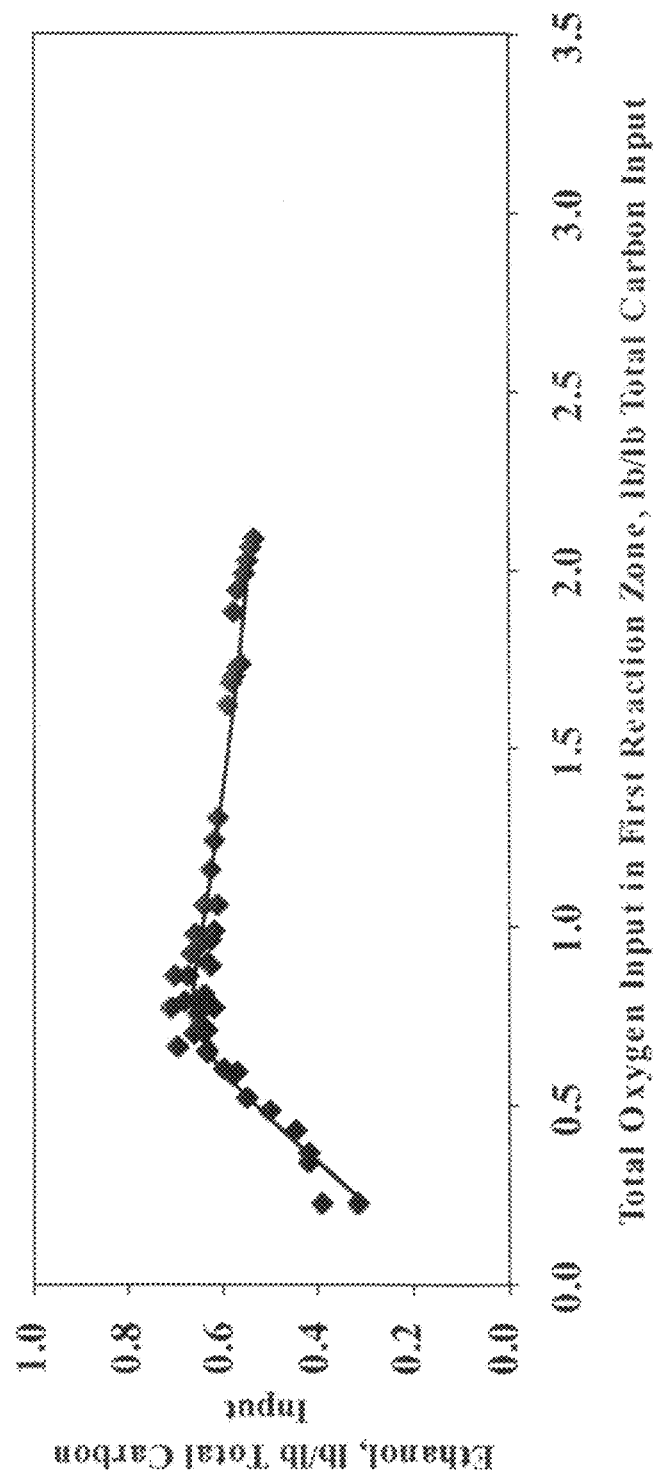
FIG. 6 comprises a schematic diagram illustrating an embodiment of the effect of total oxygen input into first reaction zone of gasifier on amount of ethanol produced for various amounts of water input into gasifier.

FIG. 6 comprises a schematic diagram illustrating an embodiment of the effect of total oxygen input into first reaction zone of gasifier on amount of ethanol produced for various amounts of water input into gasifier. As an embodiment, FIG. 6 illustrates that trend of the alcohol production initially increases with the increase in total oxygen input into first reaction zone of gasifier. FIG. 6 is a plot of ethanol produced in pounds per pound total carbon input (y-axis) versus total oxygen input in first reaction zone in pounds per pound total carbon input (x-axis). FIG. 6 is a plot of ethanol produced in pounds per pound total carbon input (y-axis) versus total oxygen input first reaction zone in pounds per pound total carbon input (x-axis); wherein total oxygen input first reaction zone is total oxygen input into first reaction zone of gasifier and total carbon input is total carbon input into gasifier. As an embodiment, FIG. 6 illustrates that trend of alcohol production initially increases with increase in total oxygen input into first reaction zone of gasifier and then decreases with increase in total oxygen input into first reaction zone of gasifier. As an embodiment, FIG. 6 illustrates that trend of ethanol production initially increases with increase in total oxygen input into first reaction zone of gasifier. As an embodiment, FIG. 6 illustrates that trend of ethanol production initially increases with increase in total oxygen input into first reaction zone of gasifier and then decreases with increase in total oxygen input into first reaction zone of gasifier. As an embodiment, FIG. 6 illustrates that trend ethanol production (pounds ethanol produced per pound of total carbon input into gasifier) increases with the increase in total oxygen input into first reaction zone of gasifier up to total oxygen input into first reaction zone of gasifier of about 0.9 pound per pound (lb/lb) total carbon input into gasifier. As an embodiment, FIG. 6 illustrates that trend of ethanol production (pounds ethanol produced per pound of total carbon input into gasifier) increases with the increase in total oxygen input in first reaction zone of gasifier up to total oxygen input in first reaction zone of gasifier of about 0.9 pound per pound (lb/lb) total carbon input into gasifier and for total oxygen input into first reaction zone of gasifier above 0.9 pound per pound (lb/lb) total carbon input into gasifier, ethanol production (pounds ethanol produced per pound of total carbon input into gasifier) decreases with increase in total oxygen input into first reaction zone of gasifier.

The foregoing descriptions of specific embodiments of the present disclosure are presented for purposes of illustration and description. They are not intended to be exhaustive or to limit the disclosure to the precise forms disclosed. Obviously, many modifications and variations are possible in view of the above teachings. While the embodiments were chosen and described in order to best explain the principles of the disclosure and its practical applications, thereby enabling others skilled in the art to best utilize the disclosure, various embodiments with various modifications as are suited to the particular use are also possible.

In one embodiment of this disclosure alcohol is produced by contacting syngas with biocatalyst in a fermentation container to produce an alcohol product mixture. In one embodiment said alcohol comprises methanol, ethanol, propanol, and butanol or their combinations. In one embodiment said alcohol comprises ethanol. In one embodiment said biocatalyst comprises acetogenic bacteria. In one embodiment said biocatalyst comprises one or more strains selected from *Clostridium*, *Moorella*, and *Carboxydothermus* or their mixed strains. In one embodiment said biocatalyst comprises one or more strains of *Clostridium ljungdahlii*. In one embodiment said *Clostridium ljungdahlii* is selected from the strains consisting of PETC, ERI-2, O-52 and C-01 or their combinations. In one embodiment said biocatalyst comprises one or more strains of *Clostridium carboxidivorans*. In one embodiment said biocatalyst comprises one or more strains of *Clostridium ragsdalei*. In one embodiment said biocatalyst comprises one or more strains of *Clostridium autoethanogenum*.

EXAMPLES

A multistage gasifier is contemplated in the present disclosure. As an embodiment, a multistage gasifier using partial oxidation method is contemplated in the present disclosure. The following examples utilize a two stage gasifier as shown in FIG. 1. The gasifier comprises a first stage or first reaction zone or lower chamber and a second stage or second reaction zone or upper chamber. Carbonaceous material is fed to the lower chamber in which air, oxygen-enriched air or pure oxygen can be injected at a controlled rate below a grate. For the examples presented below, pure oxygen is injected in the lower chamber. The lower chamber temperature and oxygen input is controlled such that only incomplete oxidation of carbonaceous material occurs, not complete combustion (also described as starved air or starved oxygen combustion). The lower chamber temperature and oxygen input is controlled such that only partial oxidation of carbonaceous material occurs, not complete combustion (also described as starved air or starved oxygen combustion). A temperature of about 650 to about 1450 degrees F. is maintained in the lower chamber. In one embodiment, a temperature of about 1400 degrees F. is maintained in the first stage. In one embodiment, a temperature less than about 1400 degrees F. is maintained in the first stage or lower chamber. The gaseous product from the lower chamber moves to the second stage or upper chamber. Ash is removed from the lower chamber. Pure oxygen is introduced into the upper chamber to raise the temperature to an upper chamber temperature in the range of about 1750 to about 3500 degrees F. in order to accomplish cracking of any tar (such as heavy hydrocarbons) contained in the gaseous stream from the first stage. Pure oxygen is introduced into the upper chamber to raise the temperature to an upper chamber temperature of about 1750 to about 3500 degrees F. in order to accomplish and partial oxidation of any tar (such as heavy hydrocarbons) contained in the gaseous stream from the first stage. For the examples presented below, the upper chamber temperature is 2250 degrees F. A raw producer gas (also called raw synthesis gas or raw syngas) containing CO, $H_2$, $CO_2$, $N_2$ and other constituents {(e.g., $O_2$, particulate matter (PM), tars, metals)} is produced and removed from upper chamber. In one embodiment, steam can be injected in the lower chamber. In an embodiment, steam can be injected in the upper chamber.

Following gasification, the producer gas is subjected to cooling and cleanup to produce a product syngas. The product syngas is introduced in a bioreactor or fermentor or fermenter to produce alcohols; methanol; ethanol; propanol; and/or butanol. In the examples below, ethanol is produced in the bioreactor.

In the examples below mathematical models were used to calculate the output of gasifier and fermenter for various process conditions and feed materials in lieu of actual experimentation. For calculation of gasifier output, a CHEMKIN mathematical model was used.

The model used a 5% air leakage into the lower chamber or first reaction zone of the gasifier.

The model for the fermentation process involves a process that converts 90% carbon monoxide and a process that converts 40% hydrogen with 95% selectivity for each process to make ethanol.

Examples 1-47

Examples 1-47 exemplify embodiment of gasification process feeding carbonaceous materials containing various amounts of water and/or co-feeding substantial amount of water or steam directly into gasifier and co-feeding landfill gas directly into gasifier. These examples exemplify embodiments of gasification process feeding single carbonaceous materials such as coal, coke oven tar (coke), plastic, tire, wood, polystyrene (PS), PETA and plurality of carbonaceous materials such as blend of biomass and vegetative waste (Biomass-VW). Relevant carbonaceous material properties, gasification conditions and product data are summarized in Tables I & II.

As embodiments, description of blends of carbonaceous materials shown in examples below:

Biomass-VW: blend of 80 wt % biomass and 20 wt % construction wood waste or vegetative waste with a 15 wt % water content of the blend Coke-fibersoft10: blend of 50 wt % coke oven tar (coke) containing no water and 50 wt % wet fibersoft containing 20 wt % water giving a 10 wt % water for the blend Coke-fibersoft20: blend of 50 wt % coke oven tar (coke) containing no water and 50 wt % wet fibersoft containing 40 wt % water giving a 20 wt % water for the blend Coke-fibersoft30: blend of 50 wt % coke oven tar (coke) containing no water and 50 wt % wet fibersoft containing 60 wt % water giving a 30 wt % water for the blend Plastic-MS W-03: blend of 90 wt % plastic containing 0.2 wt % water and 10 wt % MSW containing 30 wt % water giving a 3.2 wt % water for the blend Plastic-MSW-08: blend of 75 wt % plastic containing 0.2 wt % water and 25 wt % MSW containing 30 wt % water giving a 7.7 wt % water for the blend Plastic-MSW-15: blend of 50 wt % plastic containing 0.2 wt % water and 50 wt % MSW containing 30 wt % water giving a 15.1 wt % water for the blend Plastic-wood-04: blend of 90 wt % plastic containing 0.2 wt % water and 10 wt % wood containing 40 wt % water giving a 4.2 wt % water for the blend Plastic-wood-10: blend of 75 wt % plastic containing 0.2 wt % water and 25 wt % wood containing 40 wt % water giving a 10.2 wt % water for the blend Plastic-wood-20: blend of 50 wt % plastic containing 0.2 wt % water and 50 wt % wood containing 40 wt % water giving a 20.1 wt % water for the blend Tire-wood-00: blend of 85 wt % tire containing no water and 15 wt % wood containing 40 wt % water and then pre-dried to remove all water Tire-wood-03: blend of 85 wt % tire containing no water and 15 wt % wood containing 40 wt % water and then pre-dried to 3 wt % water content of blend Tire-wood-04: blend of 90 wt % tire containing no water and 10 wt % wood containing 40 wt % water giving a 4.0 wt % water for the blend Tire-wood-06: blend of 85 wt % tire containing no water and 15 wt % wood containing 40 wt % water giving a 6.0 wt % water for the blend Tire-wood-09: blend of 85 wt % tire containing no water and 15 wt % wood containing 40 wt % water and then added water to 9% water content of blend Tire-wood-10: blend of 75 wt % tire containing no water and 25 wt % wood containing 40 wt % water giving a 10 wt % water for the blend Tire-wood-12: blend of 85 wt % tire containing no water and 15 wt % wood containing 40 wt % water and then added water to 15% water content of blend Tire-wood-15: blend of 85 wt % tire containing no water and 15 wt % wood containing 40 wt % water and then added water to 15% water content of blend

Examples 48-57

Examples 48-52 exemplify embodiments of gasification process wherein landfill gas is introduced in the second reaction zone. Examples 53-57 exemplify embodiments of gasification process wherein landfill gas is introduced in both the first and the second reaction zones or only in the second reaction zone. Conditions and results of these examples are shown in Table III.

Examples 1-11, 48-52 and 53-57 show that co-gasification of landfill gas is beneficial for ethanol production when it is introduced in the first reaction zone or in the second reaction zone or in both the first and the second reaction zones. Examples 53-57 show that introduction of landfill gas in the lower chamber provides a small additional benefit with respect to ethanol production.

TABLE I

Properties of Carbonaceous Materials & Conditions of Gasification Processes for Examples 1-47

| | | | | | | | | | Other Feed into Gasifier, pound-moles/DT | | | | |
|---|---|---|---|---|---|---|---|---|---|---|---|---|---|
| Ex # | Carbonaceous Material | Carbonaceous Material Components, wt % | | | | | Steam in FZ | Landfill Gas in FZ | | | | $O_2$ in FZ | $O_2$ in SZ |
| | | C* | O* | H* | Ash* | Other* | Water | | $CH_4$ | $CO_2$ | $H_2O$ | Total | |
| 1 | Biomass-VW | 46.6 | 40.3 | 5.7 | 6.9 | 0.5 | 15.0 | 0.0 | 4.7 | 4.7 | 0.5 | 10 | 14.2 | 15.3 |
| 2 | Biomass-VW | 46.6 | 40.3 | 5.7 | 6.9 | 0.5 | 15.0 | 0.0 | 9.5 | 9.5 | 1.1 | 20 | 18.2 | 16.6 |
| 3 | Biomass-VW | 46.6 | 40.3 | 5.7 | 6.9 | 0.5 | 15.0 | 0.0 | 14.2 | 14.2 | 1.6 | 30 | 21.1 | 17.9 |
| 4 | Biomass-VW | 46.6 | 40.3 | 5.7 | 6.9 | 0.5 | 15.0 | 0.0 | 18.9 | 18.9 | 2.1 | 40 | 24.1 | 19.3 |
| 5 | Biomass-VW | 46.6 | 40.3 | 5.7 | 6.9 | 0.5 | 15.0 | 0.0 | 23.7 | 23.7 | 2.7 | 50 | 27 | 20.6 |
| 6 | Biomass-VW | 46.6 | 40.3 | 5.7 | 6.9 | 0.5 | 15.0 | 12.3 | 0.0 | 0.0 | 0.0 | 0 | 14 | 13.5 |
| 7 | Biomass-VW | 46.6 | 40.3 | 5.7 | 6.9 | 0.5 | 15.0 | 15.1 | 4.7 | 4.7 | 0.5 | 10 | 17.2 | 14.7 |
| 8 | Biomass-VW | 46.6 | 40.3 | 5.7 | 6.9 | 0.5 | 15.0 | 18.0 | 9.5 | 9.5 | 1.1 | 20 | 20.4 | 16 |
| 9 | Biomass-VW | 46.6 | 40.3 | 5.7 | 6.9 | 0.5 | 15.0 | 20.7 | 14.2 | 14.2 | 1.6 | 30 | 23.6 | 17.3 |
| 10 | Biomass-VW | 46.6 | 40.3 | 5.7 | 6.9 | 0.5 | 15.0 | 23.5 | 18.9 | 18.9 | 2.1 | 40 | 26.7 | 18.6 |
| 11 | Biomass-VW | 46.6 | 40.3 | 5.7 | 6.9 | 0.5 | 15.0 | 26.3 | 23.7 | 23.7 | 2.7 | 50 | 29.9 | 20 |
| 12 | Coal | 64.8 | 9.2 | 4.5 | 16.1 | 5.4 | 0.0 | 0.0 | 0.0 | 0.0 | 0.0 | 0 | 12.1 | 18 |
| 13 | Coal | 64.8 | 9.2 | 4.5 | 16.1 | 5.4 | 0.0 | 0.0 | 4.7 | 4.7 | 0.5 | 10 | 16.8 | 24 |
| 14 | Coal | 64.8 | 9.2 | 4.5 | 16.1 | 5.4 | 0.0 | 0.0 | 9.5 | 9.5 | 1.1 | 20 | 21 | 28.5 |
| 15 | Coal | 64.8 | 9.2 | 4.5 | 16.1 | 5.4 | 0.0 | 0.0 | 14.2 | 14.2 | 1.6 | 30 | 24.8 | 29.9 |
| 16 | Coal | 64.8 | 9.2 | 4.5 | 16.1 | 5.4 | 0.0 | 0.0 | 18.9 | 18.9 | 2.1 | 40 | 28.5 | 30.7 |
| 17 | Coal | 64.8 | 9.2 | 4.5 | 16.1 | 5.4 | 0.0 | 0.0 | 23.7 | 23.7 | 2.7 | 50 | 31.9 | 31.5 |
| 18 | Coke oven tar | 91.7 | 0.8 | 5.5 | 0.3 | 1.7 | 0.0 | 0.0 | 0.0 | 0.0 | 0.0 | 0 | 12.8 | 24.9 |
| 19 | Coke oven tar | 91.7 | 0.8 | 5.5 | 0.3 | 1.7 | 0.0 | 0.0 | 0.0 | 0.0 | 0.0 | 0 | 12.8 | 19.1 |
| 20 | Coke oven tar | 91.7 | 0.8 | 5.5 | 0.3 | 1.7 | 0.0 | 0.0 | 4.7 | 4.7 | 0.5 | 10 | 18.4 | 24.5 |
| 21 | Coke oven tar | 91.7 | 0.8 | 5.5 | 0.3 | 1.7 | 0.0 | 0.0 | 9.5 | 9.5 | 1.1 | 20 | 23.4 | 30.5 |
| 22 | Coke oven tar | 91.7 | 0.8 | 5.5 | 0.3 | 1.7 | 0.0 | 0.0 | 14.2 | 14.2 | 1.6 | 30 | 27.9 | 36.6 |
| 23 | Coke oven tar | 91.7 | 0.8 | 5.5 | 0.3 | 1.7 | 0.0 | 0.0 | 18.9 | 18.9 | 2.1 | 40 | 32.1 | 41.9 |
| 24 | Coke oven tar | 91.7 | 0.8 | 5.5 | 0.3 | 1.7 | 0.0 | 0.0 | 23.7 | 23.7 | 2.7 | 50 | 36 | 44.7 |
| 25 | Coke oven tar | 91.7 | 0.8 | 5.5 | 0.3 | 1.7 | 0.0 | 0.0 | 28.4 | 28.4 | 3.2 | 60 | 39.8 | 46 |
| 26 | PETA | 62.5 | 33.1 | 4.1 | 0.1 | 0.2 | 0.2 | 0.0 | 0.0 | 0.0 | 0.0 | 0 | 10 | 22.8 |
| 27 | PETA | 62.5 | 33.1 | 4.1 | 0.1 | 0.2 | 0.2 | 0.0 | 4.7 | 4.7 | 0.5 | 10 | 13.8 | 24.1 |
| 28 | PETA | 62.5 | 33.1 | 4.1 | 0.1 | 0.2 | 0.2 | 0.0 | 9.5 | 9.5 | 1.1 | 20 | 17.4 | 24.9 |
| 29 | PETA | 62.5 | 33.1 | 4.1 | 0.1 | 0.2 | 0.2 | 0.0 | 14.2 | 14.2 | 1.6 | 30 | 20.8 | 25.8 |
| 30 | Plastic | 73.0 | 10.6 | 9.5 | 3.4 | 3.5 | 0.2 | 0.0 | 0.0 | 0.0 | 0.0 | 0 | 24.3 | 29.8 |
| 31 | Plastic | 73.0 | 10.6 | 9.5 | 3.4 | 3.5 | 0.2 | 0.0 | 4.7 | 4.7 | 0.5 | 10 | 28.2 | 32.1 |
| 32 | Plastic | 73.0 | 10.6 | 9.5 | 3.4 | 3.5 | 0.2 | 0.0 | 9.5 | 9.5 | 1.1 | 20 | 32 | 33.1 |
| 33 | Plastic | 73.0 | 10.6 | 9.5 | 3.4 | 3.5 | 0.2 | 0.0 | 14.2 | 14.2 | 1.6 | 30 | 35.5 | 33.1 |
| 34 | Polystyrene | 86.7 | 4.0 | 8.4 | 0.5 | 0.4 | 0.2 | 0.0 | 0.0 | 0.0 | 0.0 | 0 | 30.7 | 30.7 |
| 35 | Polystyrene | 86.7 | 4.0 | 8.4 | 0.5 | 0.4 | 0.2 | 0.0 | 4.7 | 4.7 | 0.5 | 10 | 34.9 | 35.4 |
| 36 | Polystyrene | 86.7 | 4.0 | 8.4 | 0.5 | 0.4 | 0.2 | 0.0 | 9.5 | 9.5 | 1.1 | 20 | 38.8 | 38 |
| 37 | Polystyrene | 86.7 | 4.0 | 8.4 | 0.5 | 0.4 | 0.2 | 0.0 | 14.2 | 14.2 | 1.6 | 30 | 42.5 | 39.1 |
| 38 | Polystyrene | 86.7 | 4.0 | 8.4 | 0.5 | 0.4 | 0.2 | 0.0 | 18.9 | 18.9 | 2.1 | 40 | 46.1 | 39.9 |
| 39 | Polystyrene | 86.7 | 4.0 | 8.4 | 0.5 | 0.4 | 0.2 | 0.0 | 23.7 | 23.7 | 2.7 | 50 | 49.6 | 40.8 |
| 40 | Tire | 64.2 | 4.4 | 5.0 | 25.4 | 1.0 | 0.0 | 0.0 | 0.0 | 0.0 | 0.0 | 0 | 11.5 | 16.8 |
| 41 | Tire | 64.2 | 4.4 | 5.0 | 25.4 | 1.0 | 0.0 | 0.0 | 4.7 | 4.7 | 0.5 | 10 | 16.4 | 22.8 |
| 42 | Tire | 64.2 | 4.4 | 5.0 | 25.4 | 1.0 | 0.0 | 0.0 | 9.5 | 9.5 | 1.1 | 20 | 20.7 | 28.2 |
| 43 | Tire | 64.2 | 4.4 | 5.0 | 25.4 | 1.0 | 0.0 | 0.0 | 14.2 | 14.2 | 1.6 | 30 | 24.6 | 30.4 |
| 44 | Wood | 49.5 | 43.1 | 5.4 | 1.5 | 0.5 | 0.0 | 0.0 | 0.0 | 0.0 | 0.0 | 0 | 6.3 | 17.4 |
| 45 | Wood | 49.5 | 43.1 | 5.4 | 1.5 | 0.5 | 0.0 | 0.0 | 4.7 | 4.7 | 0.5 | 10 | 9.4 | 18.4 |
| 46 | Wood | 49.5 | 43.1 | 5.4 | 1.5 | 0.5 | 0.0 | 0.0 | 9.5 | 9.5 | 1.1 | 20 | 12.6 | 19.4 |
| 47 | Wood | 49.5 | 43.1 | 5.4 | 1.5 | 0.5 | 0.0 | 0.0 | 14.2 | 14.2 | 1.6 | 30 | 15.7 | 20.5 |

NOTE:

*indicates dry or water free basis; DT means ton of dry or water free carbonaceous material; FZ means first reaction zone; SZ means second reaction zone; FZ temperature is 1400° F.; SZ temperature is 2250° F. for all examples 1-47

TABLE II

Products of Gasification & Subsequent Fermentation Processes for Examples 1-47

| Ex # | Carbonaceous Material | Raw Syngas Components, pound-moles/DT | | | | Syngas-Carbon | Raw Syngas KSCF/DT | Ash-Carbon pound-moles/DT | Ethanol | Total O pound/pound | Total FZ O pound/pound | Ethanol Total Carbon | Syngas-Carbon pound/KSCF |
|---|---|---|---|---|---|---|---|---|---|---|---|---|---|
| | | CO | $H_2$ | $CO_2$ | $H_2O$ | | | | | | | | |
| 1 | Biomass-VW | 69.2 | 52.1 | 17.2 | 33.6 | 0.2 | 68990 | 0.574 | 13.2 | 2.06 | 1.56 | 0.58 | 0.03 |
| 2 | Biomass-VW | 75.7 | 56.6 | 20.2 | 39.2 | 0.2 | 70130 | 0.574 | 14.4 | 2.14 | 1.63 | 0.57 | 0.03 |
| 3 | Biomass-VW | 82.2 | 61.1 | 23.2 | 44.7 | 0.2 | 77271 | 0.574 | 15.6 | 2.18 | 1.66 | 0.56 | 0.03 |
| 4 | Biomass-VW | 88.6 | 65.6 | 26.1 | 50.2 | 0.2 | 84405 | 0.574 | 16.8 | 2.22 | 1.68 | 0.56 | 0.03 |
| 5 | Biomass-VW | 95.1 | 70.1 | 29.1 | 55.7 | 0.2 | 91542 | 0.574 | 18.0 | 2.25 | 1.70 | 0.55 | 0.03 |
| 6 | Biomass-VW | 59.1 | 49.3 | 17.9 | 38.8 | 0.1 | 60321 | 0.574 | 11.5 | 2.07 | 1.60 | 0.57 | 0.03 |
| 7 | Biomass-VW | 64.8 | 54.1 | 21.6 | 46.8 | 0.1 | 68488 | 0.574 | 12.7 | 2.13 | 1.65 | 0.56 | 0.02 |
| 8 | Biomass-VW | 70.6 | 58.9 | 25.3 | 54.9 | 0.1 | 76650 | 0.574 | 13.8 | 2.18 | 1.69 | 0.55 | 0.02 |
| 9 | Biomass-VW | 76.3 | 63.6 | 29.1 | 62.9 | 0.1 | 84804 | 0.574 | 14.9 | 2.23 | 1.73 | 0.54 | 0.02 |
| 10 | Biomass-VW | 82.0 | 68.4 | 32.8 | 70.9 | 0.1 | 92951 | 0.574 | 16.0 | 2.26 | 1.75 | 0.53 | 0.02 |
| 11 | Biomass-VW | 87.6 | 73.3 | 36.7 | 79.9 | 0.1 | 101499 | 0.574 | 17.1 | 2.30 | 1.77 | 0.52 | 0.02 |
| 12 | Coal | 67.5 | 42.7 | 0.1 | 0.1 | 38.9 | 55782 | 1.340 | 12.3 | 0.89 | 0.44 | 0.44 | 8.37 |
| 13 | Coal | 96.6 | 52.3 | 0.3 | 0.4 | 19.1 | 63107 | 1.340 | 17.1 | 1.17 | 0.60 | 0.56 | 3.63 |
| 14 | Coal | 118.3 | 60.6 | 1.6 | 2.1 | 5.5 | 70371 | 1.340 | 20.7 | 1.37 | 0.72 | 0.62 | 0.94 |
| 15 | Coal | 128 | 66.5 | 4.7 | 6.3 | 2.3 | 77547 | 1.340 | 22.4 | 1.48 | 0.82 | 0.63 | 0.36 |
| 16 | Coal | 134.9 | 71.7 | 8.0 | 11.1 | 1.5 | 84702 | 1.340 | 23.8 | 1.55 | 0.91 | 0.63 | 0.21 |
| 17 | Coal | 141.3 | 76.7 | 11.4 | 16.0 | 1.1 | 91850 | 1.340 | 25.0 | 1.62 | 0.98 | 0.62 | 0.14 |
| 18 | Coke oven tar | 77.9 | 61.2 | 0.1 | 0.1 | 74.9 | 78465 | 0.025 | 15.0 | 0.67 | 0.23 | 0.38 | 11.45 |
| 19 | Coke oven tar | 60.5 | 54.5 | 0.0 | 0.1 | 92.4 | 75899 | 0.300 | 12.1 | 0.57 | 0.23 | 0.30 | 14.61 |
| 20 | Coke oven tar | 91.0 | 64.4 | 0.1 | 0.1 | 71.2 | 83228 | 0.300 | 17.1 | 0.79 | 0.38 | 0.40 | 10.27 |
| 21 | Coke oven tar | 121.0 | 74.3 | 0.2 | 0.3 | 50.5 | 90555 | 0.300 | 22.0 | 1.00 | 0.50 | 0.49 | 6.69 |
| 22 | Coke oven tar | 149.9 | 83.9 | 0.5 | 0.7 | 30.8 | 97869 | 0.300 | 26.7 | 1.18 | 0.59 | 0.56 | 3.78 |
| 23 | Coke oven tar | 174.7 | 92.7 | 1.3 | 1.9 | 14.7 | 105144 | 0.300 | 30.8 | 1.32 | 0.67 | 0.62 | 1.68 |
| 24 | Coke oven tar | 190.0 | 99.7 | 3.6 | 4.9 | 6.5 | 112353 | 0.300 | 33.4 | 1.42 | 0.74 | 0.64 | 0.69 |
| 25 | Coke oven tar | 199.1 | 105.4 | 6.7 | 9.1 | 3.8 | 119531 | 0.300 | 35.0 | 1.48 | 0.80 | 0.64 | 0.38 |
| 26 | PETA | 98.6 | 40.1 | 1.4 | 1.5 | 4.4 | 53409 | 0.004 | 16.6 | 1.37 | 0.79 | 0.61 | 0.99 |
| 27 | PETA | 107.5 | 46.2 | 4.8 | 5.4 | 1.5 | 60581 | 0.004 | 18.2 | 1.49 | 0.90 | 0.61 | 0.30 |
| 28 | PETA | 113.9 | 51.6 | 8.5 | 10.0 | 1.0 | 67731 | 0.004 | 19.5 | 1.58 | 1.00 | 0.61 | 0.18 |
| 29 | PETA | 120 | 56.9 | 12.0 | 14.8 | 0.8 | 74874 | 0.004 | 20.7 | 1.66 | 1.08 | 0.60 | 0.13 |
| 30 | Plastic | 111.2 | 93.1 | 0.9 | 1.9 | 9.4 | 79625 | 0.300 | 21.7 | 1.33 | 0.68 | 0.68 | 1.42 |
| 31 | Plastic | 124.6 | 98.9 | 2.9 | 6.0 | 3.5 | 86822 | 0.300 | 24.0 | 1.46 | 0.79 | 0.70 | 0.48 |
| 32 | Plastic | 132.8 | 103.6 | 5.6 | 11.3 | 2.0 | 93985 | 0.300 | 25.5 | 1.55 | 0.88 | 0.69 | 0.26 |
| 33 | Plastic | 129.5 | 105.5 | 9.2 | 19.5 | 1.2 | 97468 | 0.300 | 25.1 | 1.61 | 0.96 | 0.64 | 0.15 |
| 34 | Polystyrene | 118.7 | 83.9 | 0.4 | 0.6 | 25.8 | 84425 | 0.038 | 22.2 | 1.18 | 0.61 | 0.59 | 3.67 |
| 35 | Polystyrene | 142.0 | 91.3 | 1.2 | 2.1 | 10.5 | 91064 | 0.038 | 26.0 | 1.35 | 0.72 | 0.65 | 1.38 |
| 36 | Polystyrene | 155.8 | 98.7 | 3.6 | 5.9 | 4.4 | 98897 | 0.038 | 28.5 | 1.46 | 0.80 | 0.67 | 0.53 |
| 37 | Polystyrene | 164.1 | 103.8 | 6.5 | 10.7 | 2.7 | 106058 | 0.038 | 30.0 | 1.53 | 0.87 | 0.67 | 0.31 |
| 38 | Polystyrene | 171.1 | 108.7 | 9.6 | 15.8 | 2.0 | 113218 | 0.038 | 31.3 | 1.59 | 0.94 | 0.66 | 0.21 |
| 39 | Polystyrene | 177.9 | 113.5 | 12.7 | 21.1 | 1.6 | 120366 | 0.038 | 32.5 | 1.64 | 0.99 | 0.65 | 0.16 |
| 40 | Tire | 58.2 | 49.4 | 0.0 | 0.1 | 46.8 | 56564 | 2.098 | 11.4 | 0.77 | 0.36 | 0.41 | 9.93 |
| 41 | Tire | 87.9 | 59.1 | 0.2 | 0.3 | 26.3 | 63880 | 2.098 | 16.3 | 1.07 | 0.53 | 0.54 | 4.94 |
| 42 | Tire | 113.6 | 68.1 | 0.9 | 1.4 | 9.3 | 71168 | 2.098 | 20.5 | 1.31 | 0.66 | 0.62 | 1.57 |
| 43 | Tire | 126.8 | 74.5 | 3.3 | 5.0 | 3.2 | 78370 | 2.098 | 22.8 | 1.43 | 0.76 | 0.65 | 0.49 |
| 44 | Wood | 75.8 | 44.9 | 6.7 | 10.2 | 0.6 | 50387 | 0.127 | 13.6 | 1.64 | 1.07 | 0.63 | 0.13 |
| 45 | Wood | 81.9 | 50.1 | 9.4 | 15.0 | 0.5 | 57273 | 0.127 | 14.8 | 1.73 | 1.17 | 0.62 | 0.10 |
| 46 | Wood | 88.3 | 54.8 | 12.6 | 20.3 | 0.4 | 64413 | 0.127 | 16.1 | 1.81 | 1.25 | 0.61 | 0.07 |
| 47 | Wood | 94.7 | 59.5 | 15.7 | 25.6 | 0.4 | 71553 | 0.127 | 17.3 | 1.88 | 1.31 | 0.60 | 0.06 |

NOTE:
DT means ton of dry or water free carbonaceous material; KSCF means 1000 standard cubic feet; FZ means first reaction zone; Total Carbon means total carbon added in gasifier that is equal to total carbon added into first reaction zone of gasifier; Total O means total oxygen added in gasifier; Total FZ O means total oxygen added in first reaction zone of gasifier

TABLE III

Data on Products of Gasification Processes for Examples 48-57 (Carbonaceous Material Feed: Biomass-VW containing 15 wt % water and containing 46.6 wt % C, 40.3 wt % O, 5.7 wt % H & 6.9 wt % ash on a dry or water free basis)

| Ex # | Other Feed in FZ, pound-moles/DT | | Other Feed in SZ, pound-moles/DT | | Ethanol pound-moles/DT |
|---|---|---|---|---|---|
| | Steam | Landfill Gas | Landfill Gas | Oxygen | |
| 48 | 12.3 | 10 | 14 | 0 | 18.8 | 12.6 |
| 49 | 12.3 | 20 | 14 | 0 | 21.5 | 14.0 |
| 50 | 12.3 | 30 | 14 | 0 | 25.5 | 15.3 |
| 51 | 12.3 | 40 | 14 | 0 | 29.6 | 16.6 |
| 52 | 12.3 | 50 | 14 | 0 | 33.6 | 17.8 |
| 53 | 0.0 | 0 | 12.3 | 50 | 34.2 | 18.2 |
| 54 | 0.0 | 10 | 15.3 | 40 | 31.4 | 18.2 |
| 55 | 0.0 | 20 | 18.2 | 30 | 28.7 | 18.1 |

TABLE III-continued

Data on Products of Gasification Processes for Examples 48-57 (Carbonaceous Material Feed: Biomass-VW containing 15 wt % water and containing 46.6 wt % C, 40.3 wt % O, 5.7 wt % H & 6.9 wt % ash on a dry or water free basis)

| Ex # | Other Feed in FZ, pound-moles/DT | | | Other Feed in SZ, pound-moles/DT | | Ethanol pound-moles/DT |
|---|---|---|---|---|---|---|
| | Steam | Landfill Gas | Oxygen | Landfill Gas | Oxygen | |
| 56 | 0.0 | 30 | 21.1 | 20 | 26.0 | 18.1 |
| 57 | 0.0 | 40 | 24.1 | 10 | 23.3 | 18.0 |
| 5 | 0.0 | 50 | 28.4 | 0 | 20.6 | 18.0 |

NOTE:
FZ means First Reaction Zone or Lower Chamber; SZ means Second Reaction Zone or Upper Chamber; DT means tons of dry or water free carbonaceous material All published documents are incorporated by reference herein. Numerous modifications and variations of the present disclosure are included in the above-identified specification and are expected to be obvious to one of skill in the art. Such modifications and alterations to the compositions and methods of the present disclosure are believed to be encompassed in the scope of the claims appended hereto. Accordingly, various modifications, adaptations, and alternatives can occur to one skilled in the art without departing from the spirit and scope herein.

We claim:

1. A method of gasification of carbonaceous materials in a gasifier to produce a product gas, said method comprising:
    adding one or more carbonaceous materials;
    adding a molecular oxygen-containing gas;
    adding a methane-containing gas; and
    optionally adding water or steam into said gasifier;
    wherein amount of total oxygen added to said gasifier in pounds per pound of total carbon added to said gasifier comprises greater than 2.0 and less than about 3.0;
    wherein the gasifier produces ash comprising ash-carbon and wherein said ash comprises less than about 10% of ash-carbon;
    wherein said product gas is produced comprising carbon monoxide, hydrogen, and tar;
    wherein said product gas is treated at a temperature of about 1750° F. to about 3500° F. in the presence of molecular oxygen to produce a raw syngas comprising carbon monoxide, hydrogen, and syngas-carbon;
    wherein said raw-syngas comprises less than about 0.5 pound syngas-carbon per 1000 SCF raw-syngas produced;
    wherein said gasifier comprises non-catalytic gasification.

2. The method of claim 1 wherein said methane-containing gas comprises: one or more gases selected from alkanes, alkenes, alkynes, landfill gas, biogas, digester gas, and natural gas.

3. The method of claim 1 further comprises:
    selection from one or more said carbonaceous material: carbonaceous liquid product, industrial carbonaceous liquid recycle, carbonaceous municipal solid waste (MSW), carbonaceous urban waste, carbonaceous agricultural material, carbonaceous forestry material, carbonaceous wood waste, carbonaceous construction material, carbonaceous vegetative material, carbonaceous petrochemical coproducts, carbonaceous coal, plastic, waste plastic, coke oven tar, fibersoft, tires, lignin, black liquor, polymers, waste polymers, polyethylene terephthalate (PETA), polystyrene (PS), sewage sludge, animal waste, crop residues, energy crops, forest processing residues, wood processing residues, livestock waste, poultry waste, food processing residues, fermentative process wastes, carbonaceous industrial waste, alcohol production wastes, ethanol coproducts, spent grains, spent microorganisms or their combinations.

4. The method of claim 1 further comprises:
    carbon content of one or more said carbonaceous materials comprising about 0.25 to about 1.0 pound per pound of one or more said carbonaceous materials on a water free basis.

5. The method of claim 1 further comprises: hydrogen content of one or more said carbonaceous materials comprising about 0.0 to about 0.25 pound per pound of one or more said carbonaceous materials on a water free basis.

6. The method of claim 1 further comprises:
    oxygen content of one or more said carbonaceous materials comprising about 0.0 to about 0.5 pound per pound of one or more said carbonaceous materials on a water free basis.

7. The method of claim 1 further comprises:
    said gasifier produces ash comprising ash-carbon and wherein said ash comprises less than about 5% of ash-carbon.

8. The method of claim 1, wherein carbon to hydrogen mass ratio in one or more of said carbonaceous material comprises 1 to 20.

9. The method of claim 1, wherein carbon to oxygen mass ratio in one or more of said carbonaceous material comprises 1 to 200.

10. The method of claim 1 further comprising:
    subjecting said raw syngas to cooling and cleaning up to produce a clean syngas;
    contacting said clean syngas with a biocatalyst in a fermentation container to produce an alcohol product mixture.

11. A method of gasification of carbonaceous materials comprising a gasifier comprising a first reaction zone and a second reaction zone, said method comprising:
    adding one or more carbonaceous materials into said first reaction zone of gasifier;
    adding a molecular oxygen containing gas, a methane-containing gas and optionally adding water or steam into one or both of said first reaction zone and second reaction zone of said gasifier;
    wherein amount of total oxygen added into said first reaction zone of said gasifier in pounds per pound of total carbon added to said gasifier comprises 2.0 to about 3.0;
    wherein optionally adding methane-containing gas in the first reaction zone of said gasifier;
    wherein said gasifier comprises non-catalytic gasification;
    producing raw syngas in said gasifier.

12. The method of claim 11 wherein said first reaction zone temperature comprises 650-1450° F.

13. The method of claim 11 wherein said second reaction zone temperature comprises 1750-3500° F.

14. The method of claim 11 further comprising:
    subjecting said raw syngas to cooling and cleaning up to produce a clean syngas;
    contacting said clean syngas with a biocatalyst in a fermentation container to produce an alcohol product mixture.

15. A method of gasification of carbonaceous materials in a gasifier comprising a first reaction zone and a second reaction zone to produce a product gas, said method comprising:
    adding one or more carbonaceous materials into said first reaction zone of gasifier;

adding a molecular oxygen containing gas, a methane-containing gas and optionally adding water or steam into one or both of said first reaction zone and second reaction zone of said gasifier;

wherein amount of total oxygen added into said first reaction zone of said gasifier in pounds per pound of total carbon added to said gasifier comprises 2.0 to about 3.0;

wherein optionally adding methane-containing gas in the first reaction zone of said gasifier;

wherein said product gas is produced comprising carbon monoxide, hydrogen, and tar;

wherein the gasifier produces ash comprising ash-carbon and wherein said ash comprises less than about 10% of ash-carbon;

wherein said product gas is raw-syngas comprising less than about 0.5 pound syngas-carbon per 1000 SCF raw-syngas produced;

wherein said gasifier comprises non-catalytic gasification.

16. The method of claim 15 wherein said first reaction zone temperature comprises 650-1450° F.

17. The method of claim 15 wherein said second reaction zone temperature comprises 1750-3500° F.

* * * * *